(12) United States Patent
Konno

(10) Patent No.: US 10,010,303 B2
(45) Date of Patent: Jul. 3, 2018

(54) IMAGE PROCESSING DEVICE, RADIATION IMAGING DEVICE, AND IMAGE PROCESSING METHOD

(71) Applicant: HITACHI, LTD., Tokyo (JP)

(72) Inventor: Yasutaka Konno, Tokyo (JP)

(73) Assignee: HITACHI, LTD., Tokyo (JP)

( * ) Notice: Subject to any disclaimer, the term of this patent is extended or adjusted under 35 U.S.C. 154(b) by 408 days.

(21) Appl. No.: 14/771,906

(22) PCT Filed: Mar. 11, 2014

(86) PCT No.: PCT/JP2014/056306
§ 371 (c)(1),
(2) Date: Sep. 1, 2015

(87) PCT Pub. No.: WO2014/156611
PCT Pub. Date: Oct. 2, 2014

(65) Prior Publication Data
US 2016/0015351 A1  Jan. 21, 2016

(30) Foreign Application Priority Data
Mar. 27, 2013 (JP) ................. 2013-066734

(51) Int. Cl.
*A61B 6/00* (2006.01)
*G06T 11/00* (2006.01)
(Continued)

(52) U.S. Cl.
CPC ............ *A61B 6/5258* (2013.01); *A61B 6/032* (2013.01); *A61B 6/035* (2013.01); *A61B 6/5205* (2013.01);
(Continued)

(58) Field of Classification Search
CPC ....... A61B 6/032; A61B 6/5258; G06T 5/005; G06T 11/005; G06T 11/006
See application file for complete search history.

(56) References Cited

U.S. PATENT DOCUMENTS

| 6,104,839 | A  | * | 8/2000 | Cok | ...................... G06T 5/20 |
| | | | | | 358/448 |
| 7,251,306 | B2 | * | 7/2007 | Sauer | ................... A61B 6/032 |
| | | | | | 378/207 |

(Continued)

FOREIGN PATENT DOCUMENTS

| JP | 11-253438 | 9/1999 |
| JP | 2009-153942 | 7/2009 |

(Continued)

OTHER PUBLICATIONS

International Search Report in PCT/JP2014/056306.

*Primary Examiner* — Thomas R Artman
(74) *Attorney, Agent, or Firm* — Cooper & Dunham LLP

(57) ABSTRACT

An image processing device or radiation imaging device for generating an image using output data from a detector for detecting a radiation transmitted through an object to be examined, wherein artifacts caused by a gap between an estimated output value and the true output value are reduced when estimating an output value of a defective element of the detector. Correction is performed not only for the output of the defective element but for the output of the surrounding normal elements used for the defective element correction by a blurring process. Additionally, whether or not to perform the blurring process for the surrounding normal elements and the degree of the blurring process are adjusted according to the device conditions, scanning conditions, and the like.

14 Claims, 15 Drawing Sheets

(51) Int. Cl.
   *A61B 6/03*   (2006.01)
   *G06T 5/00*   (2006.01)
   *G06T 7/00*   (2017.01)

(52) U.S. Cl.
   CPC .............. *A61B 6/586* (2013.01); *G06T 5/002* (2013.01); *G06T 5/005* (2013.01); *G06T 7/0012* (2013.01); *G06T 11/005* (2013.01); *G06T 2207/10081* (2013.01)

(56) References Cited

U.S. PATENT DOCUMENTS

| | | | | |
|---|---|---|---|---|
| 8,126,287 | B2* | 2/2012 | Alon | G02B 27/0012 348/240.3 |
| 8,885,076 | B2* | 11/2014 | Baron | H04N 9/045 348/241 |
| 9,552,659 | B2* | 1/2017 | Kojima | G06T 11/006 |
| 2006/0104410 | A1* | 5/2006 | Sauer | A61B 6/032 378/4 |
| 2008/0239113 | A1* | 10/2008 | Baron | H04N 5/3675 348/246 |
| 2009/0033773 | A1 | 2/2009 | Kinoshita et al. | |
| 2009/0167907 | A1 | 7/2009 | Utsugi | |
| 2015/0325012 | A1* | 11/2015 | Kojima | G06T 11/006 382/131 |
| 2016/0015351 | A1* | 1/2016 | Konno | A61B 6/032 378/4 |

FOREIGN PATENT DOCUMENTS

| | | |
|---|---|---|
| JP | 2009-164690 | 7/2009 |
| JP | 2009-201736 | 9/2009 |
| WO | WO 2007/020930 A1 | 2/2007 |

* cited by examiner

FIG.4

| | CHANNEL DIRECTION A | | | | | | | |
|---|---|---|---|---|---|---|---|---|
| SLICE DIRECTION B | 0 | 0 | 0 | 0 | 0 | 0 | 0 | 0 |
| | 0 | 0 | 0 | 0 | 0 | 0 | 0 | 0 |
| | 0 | 0 | 0 | 1 | 0 | 0 | 0 | 0 |
| | 0 | 0 | 0 | 0 | 0 | 0 | 0 | 0 |
| | 0 | 0 | 0 | 0 | 0 | 0 | 0 | 0 |
| | 0 | 0 | 0 | 0 | 0 | 0 | 0 | 0 |
| | 0 | 0 | 0 | 0 | 0 | 0 | 0 | 0 |
| | 0 | 0 | 0 | 0 | 0 | 0 | 0 | 0 |

142

FIG.8
(a)
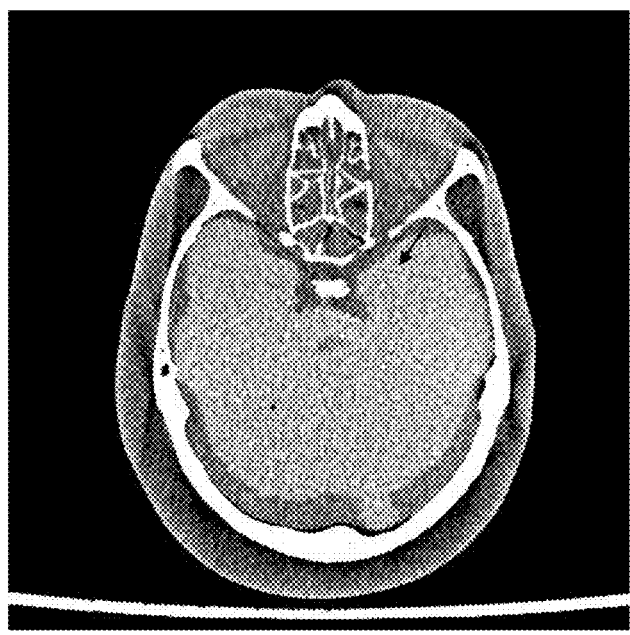
146
(b)
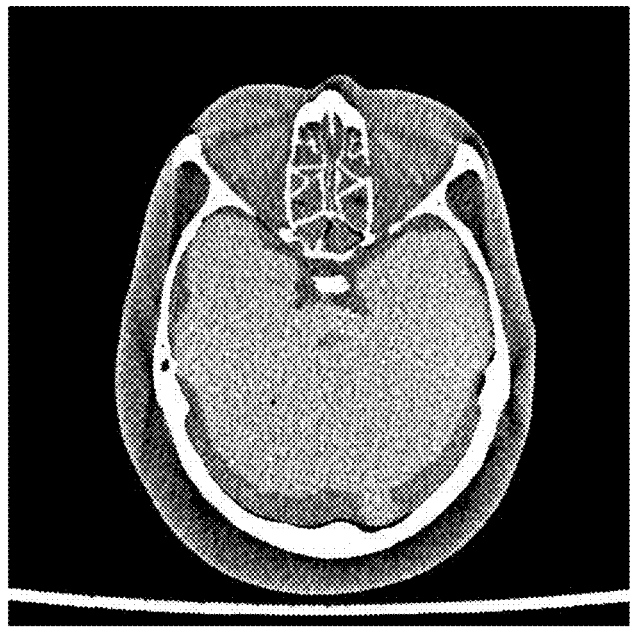
147

FIG.11
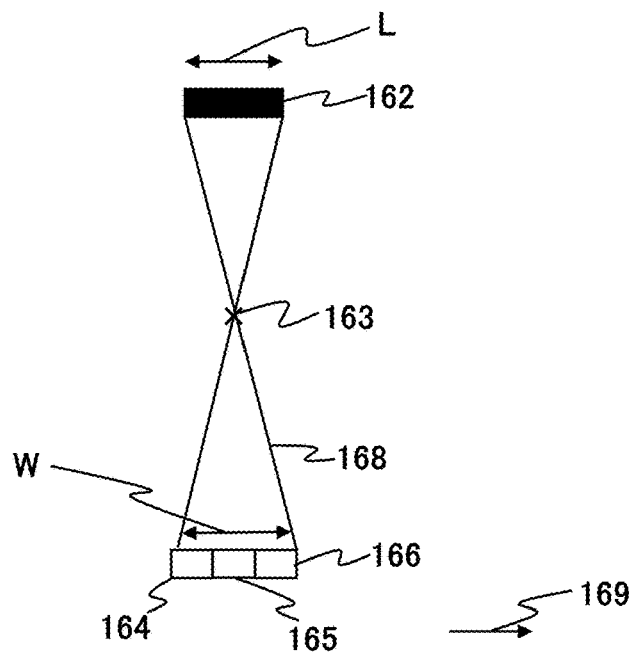
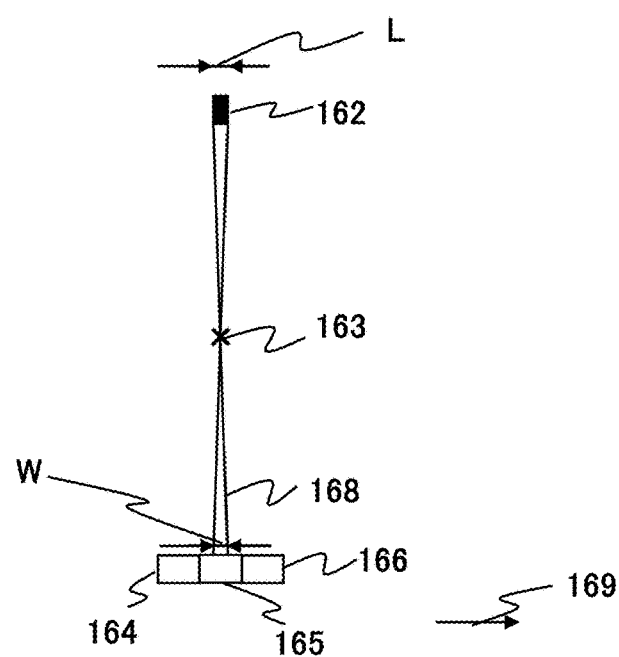

FIG.12
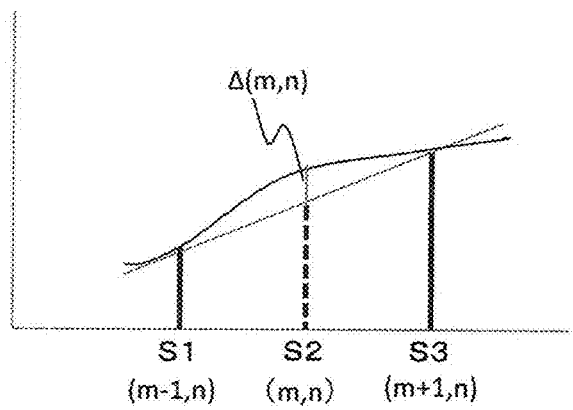
(a)
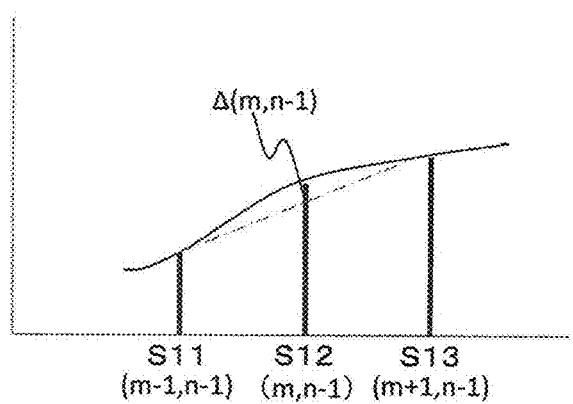
(b)
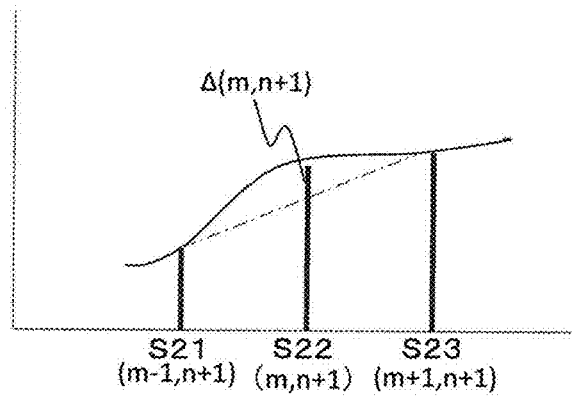
(c)

FIG.14
(a)
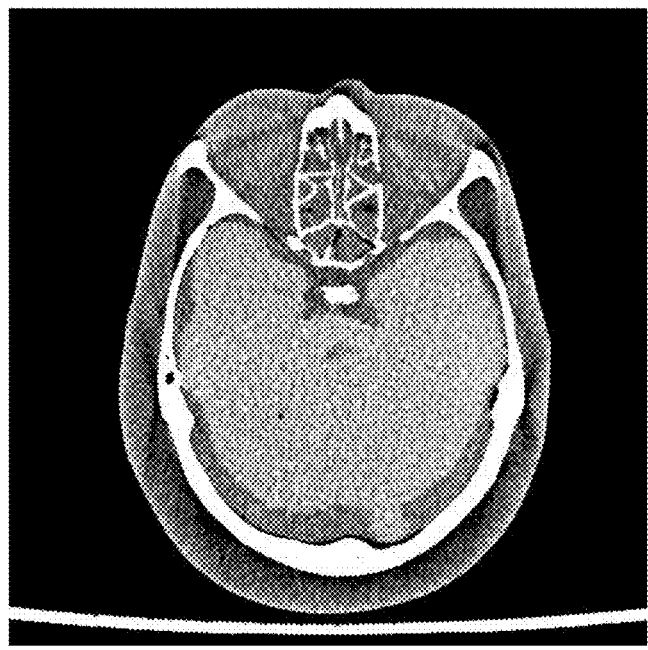
148
(b)
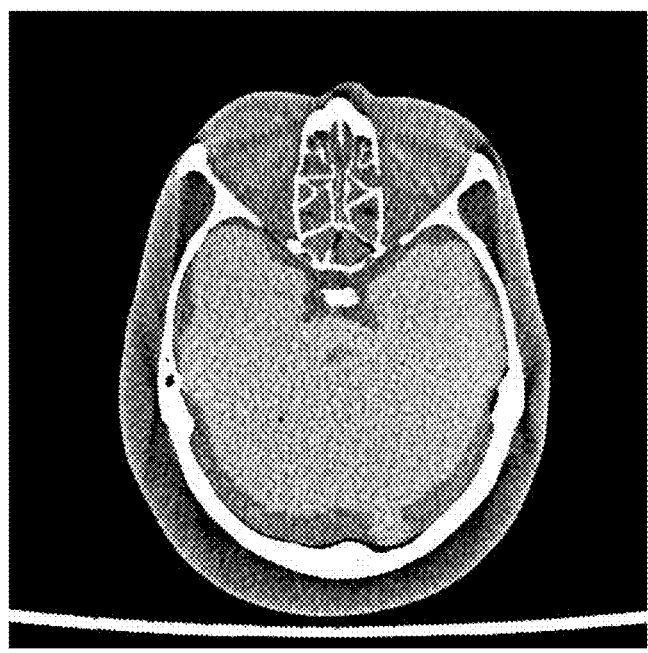
149

IMAGE PROCESSING DEVICE, RADIATION IMAGING DEVICE, AND IMAGE PROCESSING METHOD

TECHNICAL FIELD

The present invention relates to an image processing device and method for processing an image scanned by a radiation imaging device such as an X-ray CT apparatus.

BACKGROUND ART

In the medical and non-destructive examination fields, a radiation imaging device, which generates an image to be examined by oppositely disposing a radiation source and a detector in which many detection elements for detecting a radiation are arranged across an object to be examined and detecting a radiation transmitted through the object to be examined with the detector, is used widely. Particularly in the medical field, a radiation imaging device, which acquires a tomographic image of an object to be examined by rotating the radiation source and the detector around the object to be examined and using projection data scanned at various angles during the rotation, is used, and the representative example is an X-ray CT apparatus. In such a radiation imaging device, a wide range can be scanned in one rotation because a detector is provided with multiple rows in the rotation axis direction, which can shorten the scanning time.

On the other hand, as the number of detection elements increases rapidly due to the multi-row configuration of the detector, a possibility that broken detection elements (hereinafter, referred to as defective elements) can be generated is increases. The defective elements are generated due to a breakdown, manufacturing failure, and the like of a photodiode changing light to an electric signal and a reading circuit, and there are cases where the defective elements exist immediately after the device was manufactured and where the defective elements are generated as the device is used. If a detector in which the defective elements were generated is used in a CT device as is, artifacts are generated in a reconstructed image, which results in a problem of hindering diagnosis.

A sure method to remove the influence of the defective elements is to replace the defective elements and the detector therewith with the new ones. However, in addition to the cost to prepare the new detector, it requires many work steps and much of cost and time to replace a detector, to prepare detectors for replacement in advance, and the like. Also, if the defective elements are found in a clinical site, it takes much time to solve the problem, which can cause a dead time.

The other method is to perform image correction. As described in the patent literature 1, for example, this method is to set an average value of the surrounding normal elements as a correction value of a defective element for an acquired image, which can be performed easily, inexpensively, as well as immediately and is very effective. Particularly, if the defective elements are found in a clinical site, this is very effective because a dead time of the device can be reduced to the minimum.

CITATION LIST

Patent Literature

PTL 1: Japanese Patent Application Publication No. 2000-79109

SUMMARY OF INVENTION

Technical Problem

However, a correction accuracy of the defective element can be affected by conditions such as a scanned site and a device, which can cause a large difference between the correction value and the original output value (i.e., an output value in a case where the defective element is normal). Such a difference deteriorates an image of projection data composed of output values of the respective detection elements as well as causes artifacts in a tomographic image reconstructed using projection data at various angles like an X-ray CT apparatus etc.

Also, in a case where a size of a focus that is an X-ray source relatively large, the extent of a radiation to be transmitted through a predetermined part of an object to be examined is large, and the radiation enters also into detection elements around the detection elements (defective elements) on which the radiation is originally incident. Therefore, information of the radiation that is originally incident on the defective elements to be corrected is included in a value obtained by averaging the output values of these surrounding detection elements, and the accuracy as a correction value is high. Inversely, as the focus size is smaller, the correction accuracy is reduced.

The purpose of the present invention is to prevent image deterioration caused by defective elements that cannot be solved by the conventional method and prevent artifacts from appearing.

Solution to Problem

The present invention achieves the above purpose by correcting not only the output of a defective element but also the output of the surrounding normal elements used for correcting the defective element in a blurring process.

Specifically, the image processing device of the present invention comprises an image generation unit that generates an image using projection data composed of output values of the respective detection elements of a detector composed by arranging a plurality of detection elements; and a data correction unit that corrects the incompleteness of the projection data due to a defective element included in the detector, the data correction unit comprises an estimating part that estimates an output value of the defective element; and a blurring processing part that performs a blurring process for output values of the detection elements located around the said defective element using an estimated output value estimated for the defective element and sets the estimated output value as an output value for the defective element to perform correction for the detection elements using output values after the blurring process, and the image generation unit generates the image using the projection data corrected by the data correction unit.

Advantageous Effects of Invention

According to the present invention, an output value difference of defective elements is hardly found in data of a detector composed of output values of the respective detection elements. Similarly, also in a reconstructed image, artifacts caused by the output value difference of defective elements are blurred to prevent them from appearing clearly.

BRIEF DESCRIPTION OF DRAWINGS

FIG. 4 shows an example of the defective element map.

FIG. 8 shows effects of the defective element correction appearing in the reconstructed images, (a) is an image for which a blurring process is not performed, and (b) is an image for which the blurring process was performed.

FIG. 11 is a diagram explaining a relationship between a focus size and a blurring process.

FIG. 12 is a diagram explaining a gap amount of the estimated output values and the calculation method.

FIG. 14 shows effects of limiting a blurring amount appearing in the reconstructed images, (a) is an image for which limitation of a blurring amount is not performed, and (b) is an image for which the blurring amount limitation was performed.

DESCRIPTION OF EMBODIMENTS

Hereinafter, the embodiments of the present invention will be described.

The radiation imaging device of the present embodiment comprises a radiation source, a detector that is placed opposite to the said radiation source and composed by arranging a plurality of detection elements, an image generation unit that generates an image to be examined using projection data composed of output values of the respective detection elements of the detector, and a data correction unit that corrects the incompleteness of the projection data due to a defective element included in the detector.

The data correction unit comprises an estimating part that estimates an output value of the defective element included in the detector and a blurring processing part that performs a blurring process for output values of first adjacent elements located adjacent to the said defective element using an estimated output value estimated for the defective element and sets the estimated output value and an output value after the blurring process as a corrected output value respectively for the defective element and the first adjacent elements. The image generation unit generates the image using the projection data corrected by the data correction unit.

One form of the radiation imaging device of present embodiment further comprises a rotating plate for rotating the radiation source and the detector around an object to be examined, and projection data composed of output values of the respective detection elements includes a plurality of projection data having different positions in the rotation direction of the detector. The image generation unit comprises a data correction section that corrects deficiency of the projection data caused by a defective element included in the detector and a reconstruction section that reconstructs the image using the corrected projection data, and the data correction section includes the above estimating part and the blurring processing part as well as sets an estimated output value and an output value after the blurring process as a corrected output value respectively for a defective element and first adjacent elements.

Hereinafter, the embodiments of the present invention applied to the X-ray CT apparatus will be described in detail by referring to the diagrams.

Figure 1:
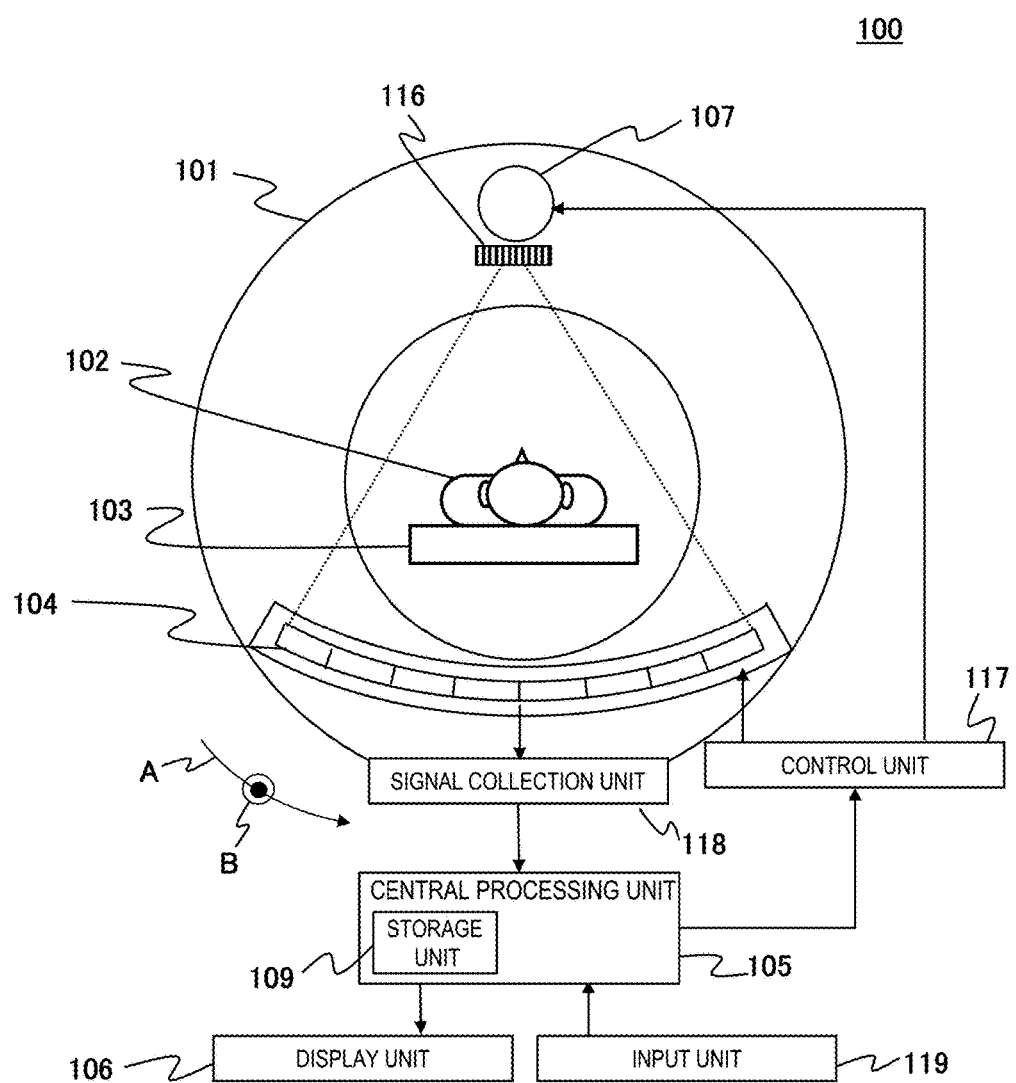
FIG. 1 is a schematic diagram of the X-ray CT apparatus to which the present invention is applied.
Figure 2:
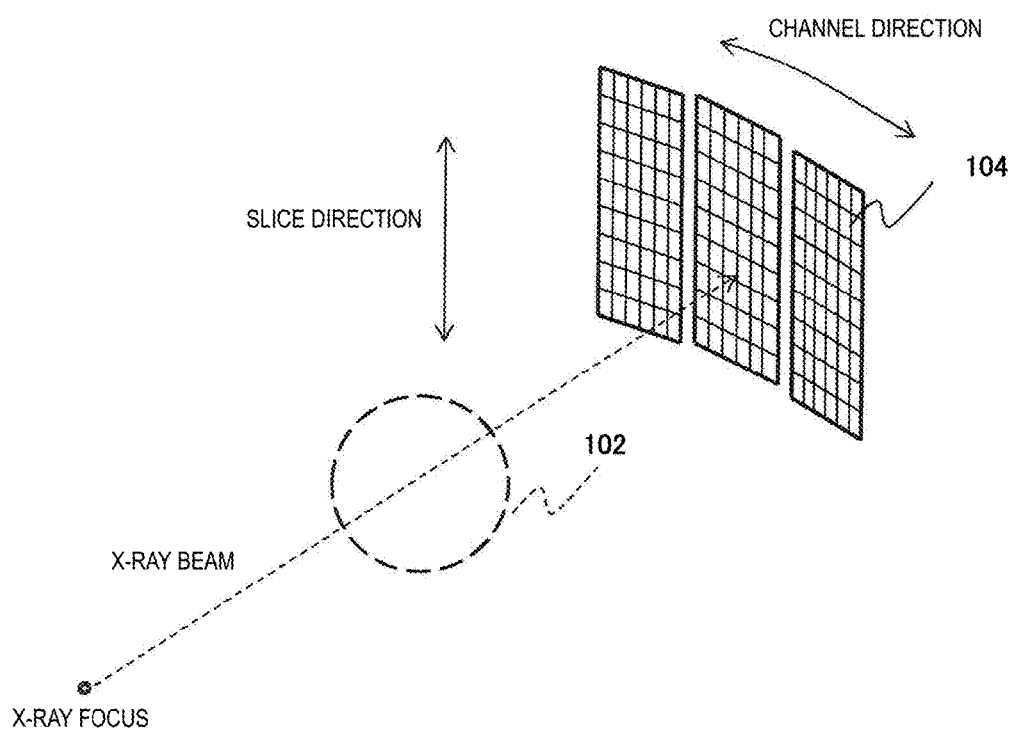
FIG. 2 shows a configuration example of the X-ray detector.

FIG. 1 is a schematic diagram of the X-ray CT apparatus to which the present invention is applied, and FIG. 2 shows a configuration example of the X-ray detector.

The overview of the X-ray CT apparatus 100 of the present embodiment will be described using FIG. 1. The X-ray CT apparatus 100 of the present embodiment is mainly composed of the X-ray source 107, the X-ray collimator 116, the X-ray detector 104, the signal collection unit 118, the central processing unit 105, the display unit 106, the input unit 119, the control unit 117, the storage unit 109, the gantry rotation unit 101, and the bed top plate 103. A plurality of the X-ray detectors 104 are arranged in an arc-shaped manner approximately centering the X-ray source 107 and is installed in the gantry rotation unit 101 together with the X-ray source 107.

Although the indication is omitted in FIG. 1, the X-ray grid is provided in front of the X-ray detector 104 and prevents an X-ray scattered by the object 102 etc. from being incident on the X-ray detector 104 from among X-rays irradiated from the X-ray source.

The X-ray detector 104 has a structure where X-ray detection elements that are composed of a scintillator converting an X-ray into a light and a photodiode converting a light from the scintillator into an electrical charge are arranged two-dimensionally in the channel and slice directions as shown in FIG. 2 and can acquire an electrical charge amount according to the incident X-ray. The X-ray detectors 104 are arranged so that the channel direction of the X-ray detection elements corresponds to the rotation direction (the arrow A in FIG. 1) of the X-ray detectors 104 and the slice direction corresponds to the rotation axis direction (B in FIG. 1). Additionally, although FIG. 1 shows a case of eight X-ray elements in the channel direction and FIG. 2 shows only three of the X-ray detectors 104 to simplify the explanation, the actual device has, for example, approximately 40 pieces of the X-ray detectors.

Next, the scanning method to acquire a reconstructed image (hereinafter, described as actual scanning) and the image processing method using this X-ray CT apparatus will be described. First, the start of actual scanning is input from the input unit 119, and then an X-ray is irradiated from the focus of the X-ray source 107. The irradiation field of the X-ray is limited by the X-ray collimator 116, the X-ray is irradiated to the object 102 placed on the bed top plate 103, and then the X-ray transmitted through the object 102 is detected by the X-ray detectors 104.

This scanning repeatedly changes an irradiation angle of the X-ray to the object 102 by rotating the gantry rotation unit 101 in the rotation direction A to acquire projection data of 360 degrees. Hereinafter, the irradiation angle to acquire the projection data is referred to as a viewing angle. Scanning is performed for a plurality of views by 0.4 degrees.

An electrical charge amount obtained thus is collected in the signal collection unit 118 and converted into a digital signal to generate raw data. Next, a correction process is performed for the raw data in the central processing unit 105 to generate projection data. Then, reconstruction is performed to generate a reconstructed image of the X-ray absorption coefficient distribution of the object 102. The result is displayed on the display unit 106.

Figure 3:
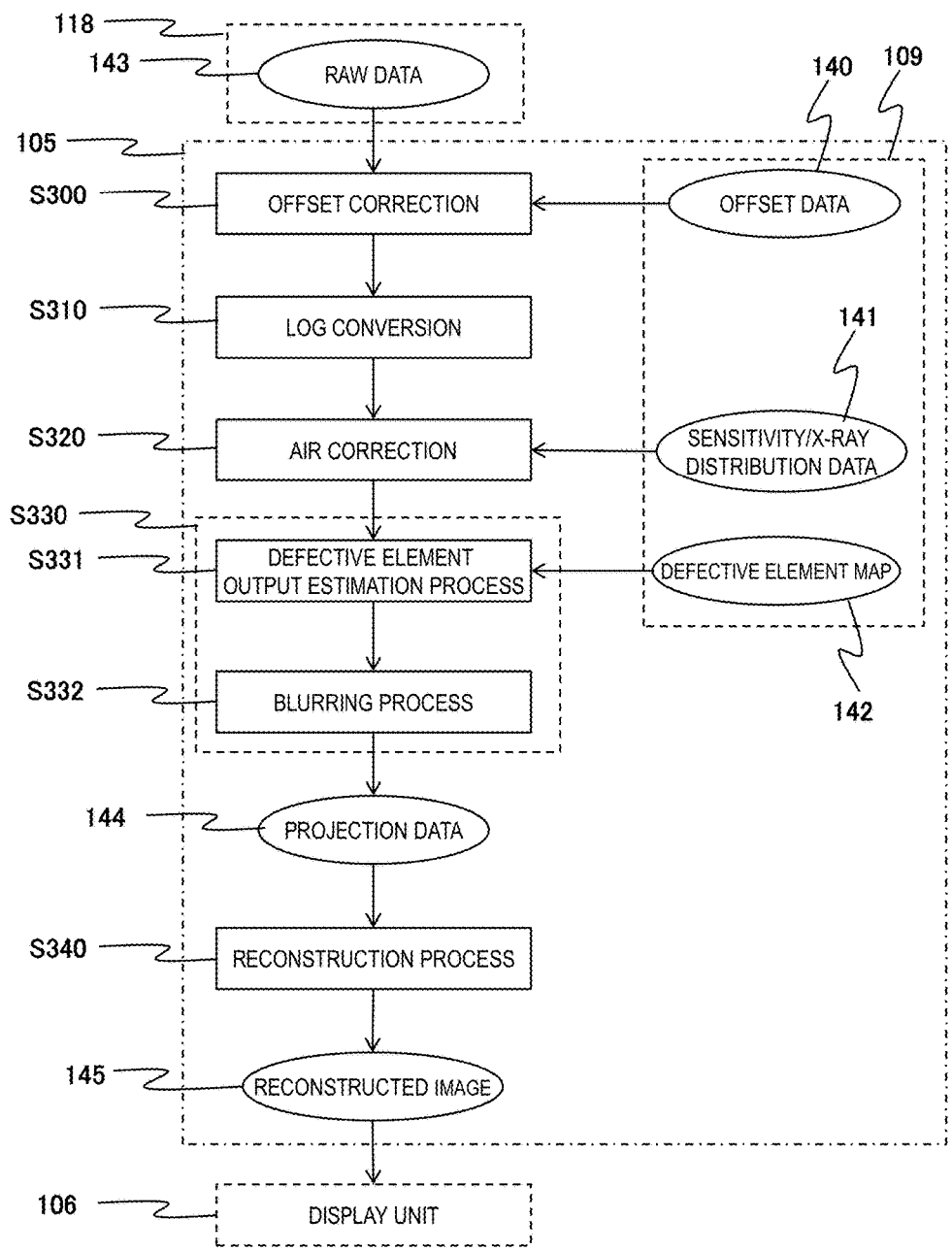
FIG. 3 is a flow showing the correction process procedure.

Next, the correction process to be performed by the central processing unit 105 will be described in detail using the flow of FIG. 3. The correction process to be performed includes, for example, the offset correction S300 for correcting the zero level of the X-ray detectors 104, the air correction S320 for correcting sensitivity distribution of the X-ray detectors 104 and X-ray irradiation distribution, and the defective element correction S330 for estimating an output value of a defective element. Here, the correction process of FIG. 3 is just an example and does not limit the present invention. For example, there can be cases where the order of these corrections is different, where the other correction is added, and where there are no corrections other than the defective element correction S330.

First, the central processing unit 105 performs the offset correction S300 for the raw data 143 received from the signal collection unit 118. This correction is achieved by, for example, differentiating the offset data 140 generated before actual scanning and stored in the storage unit 109 from the raw data. The offset data 140 is zero-level data and, for example, is generated by acquiring raw data without irradiating an X-ray and performing a weighted average process for the data for a view.

Next, the LOG conversion S310 is performed. In a case where a value before the conversion is X and that after the conversion is Y, the LOG conversion is expressed by the formula (1), for example. Here, a and b are constant coefficients

[Formula 1]

$$Y=a \text{ LOG}(X)+b \tag{1}$$

Next, the air correction S320 is performed. This correction is achieved by, for example, differentiating the sensitivity/X-ray distribution data 141 generated before actual scanning and stored in the storage unit 109 from the raw data after the LOG conversion S310. The sensitivity/X-ray distribution data 141 is, for example, generated by irradiating an X-ray from the focus of the X-ray source 107 to acquire raw data without providing the object 102 and performing the offset correction S300 for the data, the weighted average process for a view, and the LOG conversion.

Next, the defective element correction S330 is performed. The defective element correction S330 is performed to prevent artifacts from being generated in a reconstructed image due to a defective element included in the detector and includes the defective element output estimation process (hereinafter, referred to also as an estimation process) S331 for estimating an output value of the defective element and the blurring process S332 for changing the output of normal elements around the defective element. The corrections from S300 to S330 may be achieved by being stored as a program in a computer hard disk, storage media, and the like by the central processing unit 105 or may be achieved by an electrical circuit. The central processing unit 105 and the electrical circuit for performing the correction processes are referred to as a data correction unit, a defective element output estimation processing part (estimation part), and a blurring processing part in the present description.

After acquiring projection data 144 by performing the processes as described above, the reconstruction process S340 is performed to generate the reconstructed image 145. Finally, the reconstructed image 145 is displayed on the display unit 106.

The X-ray CT apparatus of the present embodiment is characterized by the defective element correction due to a defective element included the X-ray detectors 104 from among the above correction processes, and there are various methods as a defective element output estimation processing method and a blurring processing method. Hereinafter, a representative embodiment of the defective element correction will be described in detail.

<First Embodiment>

The present embodiment calculates an estimated output value of the said defective element using output values of the first adjacent elements located around the defective element in the estimation process and calculates a blurring amount using at least either one of an estimated output value estimated for the defective element or output values of the second adjacent elements other than the defective element that are located around the first adjacent elements in the blurring process to be performed by adding the blurring amount to the output values of the first adjacent elements. More specifically, the blurring process is performed using a value for which a first blurring rate is multiplied by an estimated output value estimated for the defective element, output values of the first adjacent elements, and a value for which a second blurring rate is multiplied by output values of the second adjacent elements other than the defective element that are adjacent to the first adjacent elements.

«Defective Element Output Estimation Process»

First, in the defective element output estimation process S331, defective element information of the defective element map 142 stored in the storage unit 109 is acquired, and then an estimation process is performed for an element in a position registered on the map. An example of the defective element map 142 is shown in FIG. 4. In the diagram, 0 and 1 show a normal element and a defective element respectively. In FIG. 4, eight elements in the channel direction A and eight elements in the slice direction B exist two-dimensionally, and a case where there is a defective element in the position of the fourth channel and the third slice. However, the number of elements, the position of the defective element, and the defective element map are just examples and do not limit the present invention.

The defective element map 142 is generated before scanning and stored in the storage unit 109. For the map generation, an image in which an X-ray was irradiated without providing an object and an image in which irradiation was not performed are acquired for example, and then an element whose output change amount is remarkably larger or smaller than an average change amount of all elements is determined as a defective element. However, this determination method for a defective element is just an example and does not limit the present invention.

Next, an estimated output value of the defective element is calculated using output values of the normal elements around the defective element (elements other than the defective element). First, a case where the defective element is not an end channel will be described.

Figure 5:
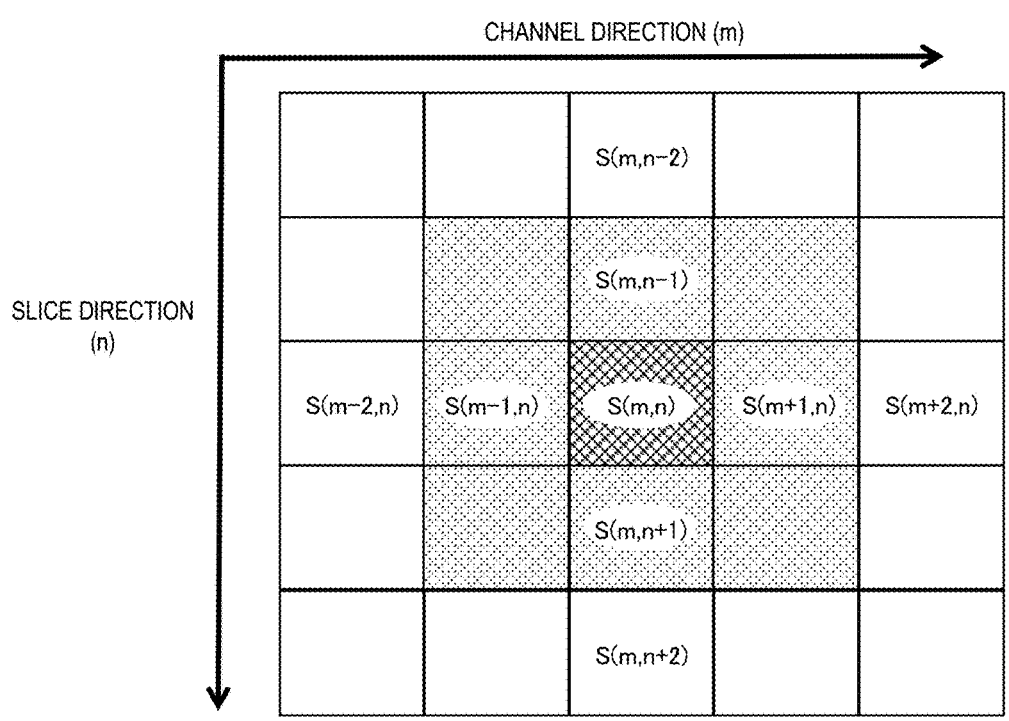
FIG. 5 shows a relationship between a defective element and the surrounding elements used for correction.

When this defective element is the m-th in the channel direction and the n-th in the slice direction, m is an integer equal to or more than 2, and n is a natural number. FIG. 5 shows the 5×5 detection element arrangement where a defective element S(m, n) is centered. There are eight elements around this defective element S(m, n), and an estimation process can be performed using at least any one of the output values of these eight elements (normal elements).

Figure 6:
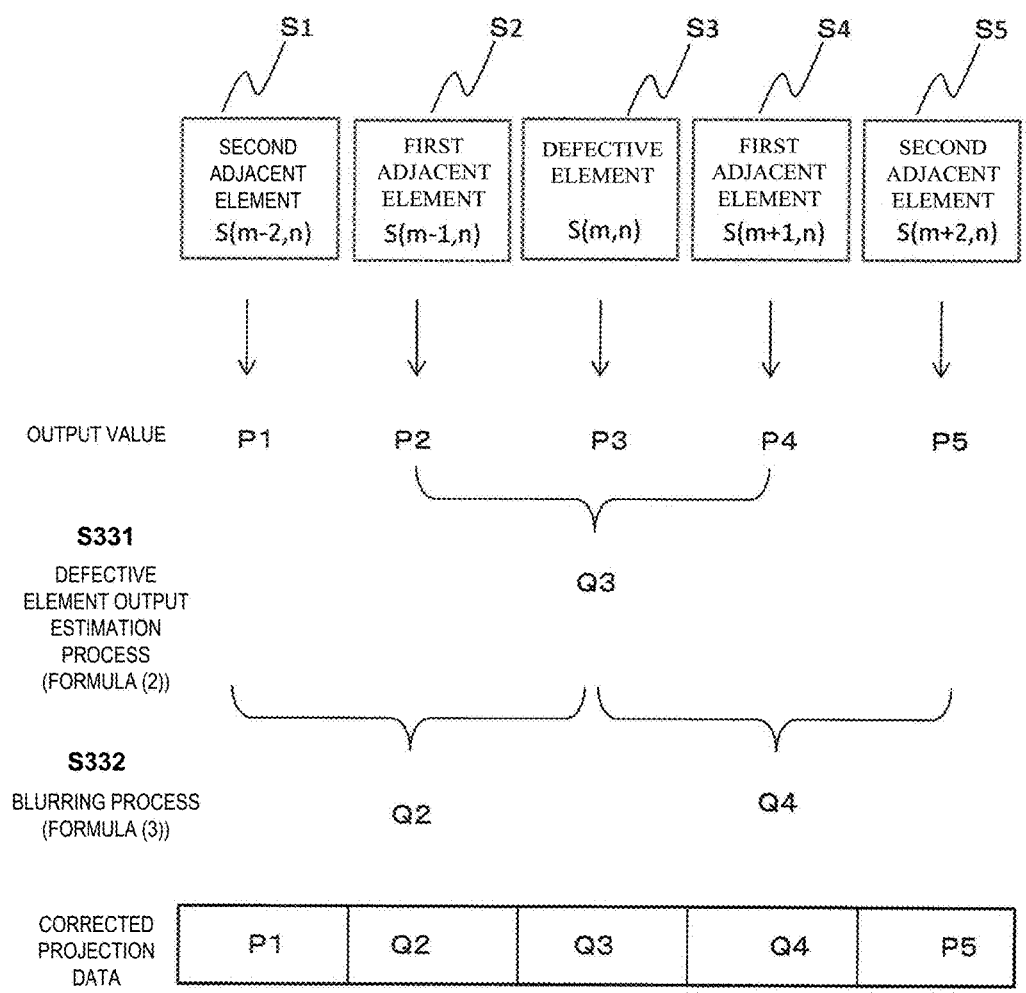
FIG. 6 is a diagram explaining an example of the defective element correction.

For example, two normal elements adjacent to both the sides in the channel direction or slice direction, two normal elements adjacent to both the sides in an oblique direction or the combination can be used. As an example, a case of estimating an output value of a defective element S(m, n) is described below using the output values of two normal elements S(m+1, n) and S(m−1, n) adjacent in the channel direction. The overview of the process is shown in FIG. 6. FIG. 6 shows the defective element S(m, n) as S3 and shows the two elements S(m−1, n) and S(m+1, n) adjacent in the channel direction as S2 and S4.

When the output values of the elements S2 and S4 adjacent to the defective element S3 are set as P(m+1, n) and P(m−1, n) respectively, an estimated output value Q(m, n) of the defective element S3 can be estimated by the formula (2).

[Formula 2]

$$Q(m,n) = \frac{1}{2}(P(m-1,n) + P(m+1,n)) \quad (2)$$

In the estimation process S331, this estimated output value Q(m, n) is set as an output value of the defective element S3. Additionally, although the formula (2) calculates an estimated output value by linear interpolation, the estimated output value calculation may be performed using not only the linear interpolation but various non-linear interpolations such as a polynomial or a function determined by function fitting using adjacent elements.

When a defective element is an end channel (the first channel or the M-th channel, M is the total number of channels here.) and when either of the adjacent elements does not exist, the estimated output value can be calculated also by extrapolating from an output value of one element adjacent in the channel direction or from output values of an element adjacent to the defective element and an element adjacent to the adjacent element. Alternatively, instead of the element adjacent in the channel direction, output values of the elements S(M, n+1) and S(M, n−1) adjacent in the slice direction may be used or output values of elements adjacent in the channel direction and elements adjacent in the slice direction may be used.

In a case where adjacent elements to a defective element are also defective elements, similarly to a case where a defective element is at the end of the detector, an estimation process can be performed using the output values of the surrounding normal elements alone or in combination.

«Blurring Process»

Next, the blurring process S332 is a process to correct image deterioration caused by a gap between an estimated output value of the defective element estimated by the above estimation process S331 and the true output value (that should be acquired if there is no defect) and is performed for elements adjacent to the defective element for which the estimation process was performed (hereinafter, described as a first adjacent element). The first adjacent elements for which the blurring process is performed are elements forming a reconstructed image same as the defective element in the reconstruction process, and are, for example, elements adjacent to the defective element in the channel direction. As an example, a case where the elements S2 and S4 adjacent in the channel direction shown in FIG. 6 similarly to the estimation process are the targets to be processed will be described below.

In the present embodiment, the output values after a blurring process (corrected output values) Q2 of the first adjacent elements S2 are determined using the output values P2 of the first adjacent elements S2, the output values P1 of the elements S1 adjacent to the first adjacent elements S2 (hereinafter, described as a second adjacent element), and the estimated output value Q3 of the defective element S3 after the estimation process S331. Similarly, the output values after a blurring process (corrected output values) Q4 of the first adjacent elements are determined using the output values P4 of the first adjacent elements S4, the output values P5 of the second adjacent elements S5 adjacent to the first adjacent elements S4, and the estimated output value Q3 of the defective element S3 after the estimation process S331. Here, although the defective element S3 for which the estimation process S331 is performed is adjacent to the first adjacent elements S2 and S4, the defective element S3 is not included in "the second adjacent elements" in order to distinguish from the second adjacent elements S1 and S5.

When a first adjacent element is not in an end channel, corrected output values Q(m−1, n) and Q(m+1, n) of the two first adjacent elements S2 and S4 can be calculated in the formula (3) by setting a blurring rate as α, for example.

[Formula 3]

$$Q(m+i, n) = \frac{P(m+i, n) + \alpha P(m+2i, n) + \alpha Q(m, n)}{1 + 2\alpha} \quad (i = \pm 1) \quad (3)$$

In the formula (3), "i=+−1" means that both cases of 1 and −1 are applied. This is similar also in the following descriptions.

A blurring rate α can be determined by considering a gap between an estimated output value and a true value of a defective element. As described above, a blurring process is a process for reducing artifacts caused by the gap by slightly blurring the surroundings of the defective element locally if the estimated output value of the defective element has a gap (error). The larger the blurring rate α is, the more the visibility of the artifacts can be reduced. However, if the blurring rate α becomes too large, new artifacts are generated by the blurring process S332. Therefore, for example, an object such as a phantom is scanned in advance, the defective element output estimation process S331 and the blurring process S332 are applied after changing the blurring rate α, and then an artifact amount is evaluated to determine an optimal blurring rate α before actual scanning.

When the first adjacent elements adjacent to a defective element are located at the end in the channel direction, a corrected output value after a blurring process may be calculated from output values of the first adjacent elements and an estimated output value of the defective element. For example, when the (m+j) channel (j=1 or −1) where there are the first adjacent elements is an end channel, a corrected output value Q(m+j, n) of the first adjacent elements of the end channel is calculated as shown in the formula (4).

[Formula 4]

$$Q(m+j, n) = \frac{P(m+j, n) + \alpha Q(m, n)}{1 + \alpha} \quad (4)$$

Figure 7:
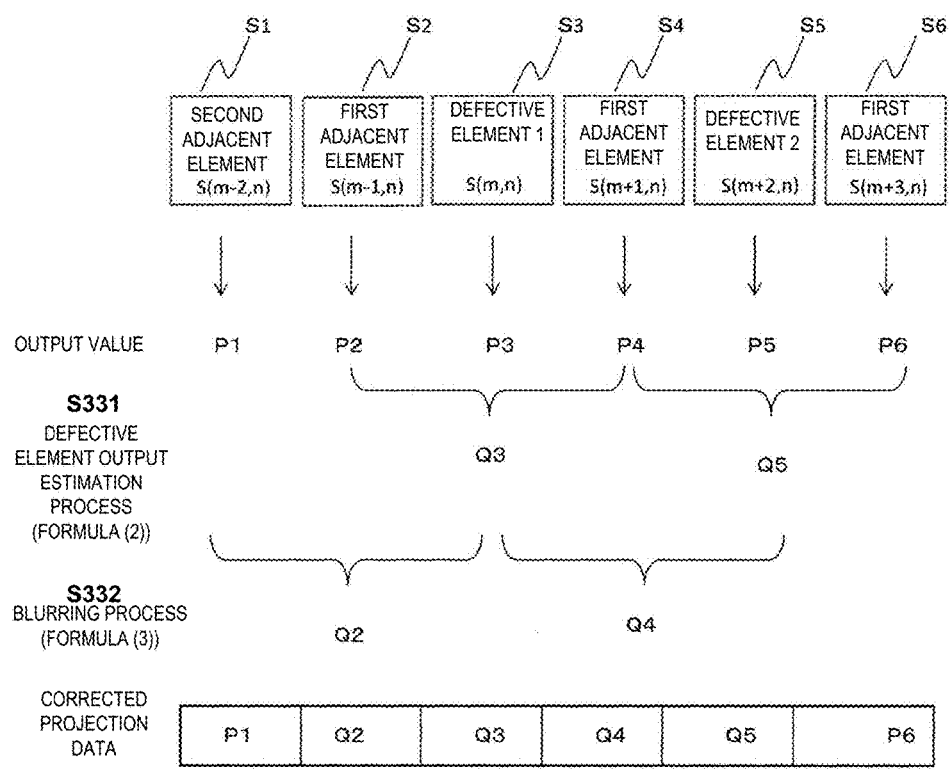
FIG. 7 is a diagram explaining the other example of the defective element correction.

Additionally, as shown in FIG. 7, when a second adjacent element is a defective element (the defective element 2), an estimation value Q(m+2i, n) of the second adjacent element calculated in the defective element output estimation process S331 may be used instead of an output value P(m+2i, n) of the second adjacent element of the formula (3). In the example shown in FIG. 7, the output value P4 of the first adjacent element S4, the estimated output value Q3 of the defective element S3, and the estimated output value Q5 of the defective element S5 are used in order to calculate a corrected output value of the first adjacent element S4 adjacent to the defective element S3. Thus, in a case where there are a plurality of defective elements, the blurring process S332 can be achieved even if the second adjacent element is a defective element by performing the blurring process S332 after performing the defective element output estimation process S331 for all the defective elements.

Additionally, although a corrected output value Q(m+1, n) of a first adjacent element was calculated from an estimated output value Q(m, n) of a defective element, an output value P(m+i, n) of a first adjacent element, and an output value P(m+2i, n) of a second adjacent element in the formula (3), this is just an example, and for example, the blurring process S332 may be performed without using either of an estimated output value Q(m, n) of the defective element or an output value P(m+2i, n) of the second adjacent element. Also, the blurring process can be performed using output values of the other elements.

Also, in the above blurring process, a corrected output value of a first adjacent element was calculated using weighted addition of the formulas (3) and (4), a function used for the blurring process is not limited to this, and various functions can be used. At this time, a corrected output value Q(m+i, n) of the first adjacent element can be expressed by the formula (5) by generalizing the function as "f".

[Formula 5]

$$Q(m+i,n)=f(P(m+i,n),P(m+2i,n),Q(m,n)) \quad (5)$$

After the correction is performed until the defective element correction S330 (the output estimation process S331 and the blurring process S332) described above, an estimated output value or a corrected output value is set as a pixel value for elements to be estimated and corrected in the defective element correction S330, and an output value is set as a pixel value for the other elements to be stored as the projection data 144 as shown in FIG. 3 (See FIG. 3). Since a plurality of projection data with different view angles can be acquired in an X-ray CT apparatus, the defective element correction S330 described above is performed for the plurality of the projection data. Next, the reconstruction process S340 such as a convolution I performed for the corrected projection data to generate the reconstructed image 145 of the object 102, and then the image is displayed on the display unit 106.

According to the present embodiment, if artifacts are generated because an estimated output value of a defective element has a gap (error) by performing the blurring process S332 for the first adjacent elements located around the defective element, the surroundings are also slightly blurred locally, which can reduce the artifacts. As an example, the shown in FIG. 8 are the reconstructed images 146 and 147 of the head phantom in the case (a) of not performing the blurring process of the formula (3) and in the case (b) of performing the blurring process (the blurring rate α: 0.5) after performing the defective element output estimation process of the formula (2). These images are generated according to whether or not the blurring process S332 was performed after generating a pseudo defective element for the raw data 143 without a defective element acquired by scanning with the X-ray detector 104. It is found that the artifacts shown by the arrow in the image 146 are reduced in the image 147, and the effect of the blurring process S332 can be seen.

Thus, according to the present embodiment, even in a case where there is a defective element, the reconstructed image 145 in which there are no artifacts due to the defective element or in which the artifacts are reduced can be obtained.

As described above, although an output estimation process of a defective element and a blurring process for the output of the surrounding normal elements are mainly described in the first embodiment, various changes can be added to specific contents of the output estimation process and the blurring process, and the order etc. can be changed as needed. Hereinafter, the change example of the first embodiment will be described.

<Change Example of First Embodiment>

«Change Example of Defective Element Output Estimation Process»

Although an estimated output value is calculated using an output value of an element adjacent in the channel direction in the first embodiment, an output of not only an adjacent element but also an element located across one or more elements from a defective element may be used. Selecting such an element is useful particularly in cases where an adjacent element is also a defective element and where two or more defective elements are adjacent. Also, an interpolation method and an element to be used for estimation may be changed according to the position of the defective element and the other factors.

Figure 9:
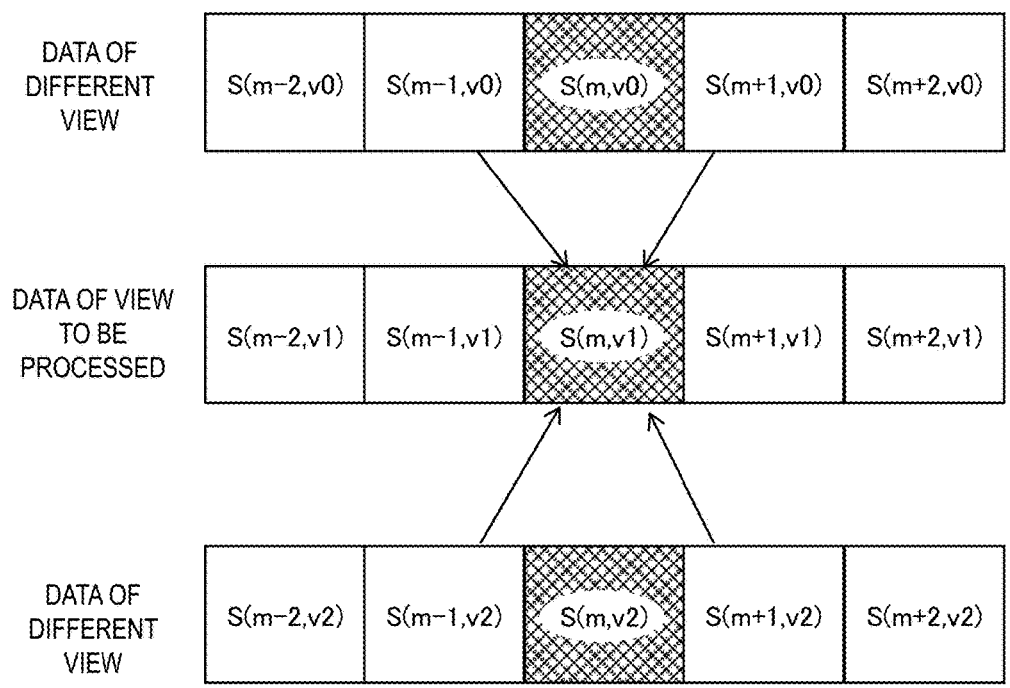
FIG. 9 shows an example of the defective element correction using output values of different views.

Although a case where output values of a defective element that is a target of an estimation process and an adjacent element used for the estimation process are those of the same view is described in the first embodiment, output values of different views can also be used for the estimation process. For example, one or more output values of projection data acquired in a different rotation period even at the same view angle and data with different view angles can be used. FIG. 9 shows an example of using data with different angles. Additionally, FIG. 9 shows an element position using S (channel, view) that is a format different from FIG. 5.

In this example, an estimated output value of a defective element S(m, v1) in a target view (view of an angle v1) is calculated using an output value of a first adjacent element of a past view (view of an angle v0) obtained before or an output value of a first adjacent element of a future view (view of an angle v2) obtained thereafter. Although an output value of the same slice is used in this case, an output value of a different slice may be used. Additionally, in a case of using a plurality of output values, output values of different views may be used. However, in a case of using the different views, it is desirable that each view angle difference is equal to or less than approximately 5 degrees.

«Change Example 1 of Blurring Process»

Although a case where signals are added by setting the same blurring rate α of adjacent elements on both the sides is shown using the formula (3) as the blurring process S332 in the first embodiment, different blurring rates can be used. For example, by setting a blurring rate of an output value of a second adjacent element as $\alpha_1$ and a blurring rate of an output value of a defective element as $\alpha_2$ ($\alpha_1 \neq \alpha_2$), an output value of a first adjacent element may be calculated by the formula (6).

[Formula 6]

$$Q(m+i,n) = \frac{P(m+i,n) + \alpha_1 P(m+2i,n) + \alpha_2 Q(m,n)}{1+\alpha_1+\alpha_2} \quad (6)$$

$(i = \pm 1)$

«Change Example 2 of Blurring Process»

The signal addition is not performed for each defective element at a certain blurring rate, but the blurring rate may be changed according to the defective element position and the output value. As an example of changing a blurring rate according to the defective element position, the blurring rate is changed according to the distance from the rotation center. Specifically, since an element closer to the rotation center generates artifacts due to a small error compared to a further element, the blurring rate becomes larger when the element is closer to the rotation center, and the blurring rate becomes smaller when the element is further from the rotation center.

Also, a blurring rate may be changed depending on a correction value of a defective element, an output value of the first adjacent element, correction values and output values of the surrounding elements etc. of a first adjacent element, a change amount in the view direction of those correction values and output values, a change amount in the channel and slice directions, and the like. An example of the change amount is noise or SNR. Therefore, the blurring rate can be set according to the object structure or the visibility of artifacts varying depending on an output level, noise level, and the like of a reconstructed image. By thus adjusting the blurring rate, unnecessary blurs are reduced, which can reduce the artifacts sufficiently.

«Change Example 3 of Blurring Process»

Although the first embodiment calculates a corrected output value of a first adjacent element from an estimated output value of a defective element, an output value of the first adjacent element, and an output value of a second adjacent element in the same view in the blurring process S332, an output value or estimation value of different views can also be used for the blurring process as estimated from the change example of the estimation process using FIG. 9. For example, a corrected output value of a first adjacent element in projection data of a predetermined view may be calculated using an estimated output value of the same defective element, an output value of the first adjacent element, and an output value of the second adjacent element calculated for projection data of a view obtained before the said view (past view) and a view obtained thereafter.

Additionally, there can be a case where a plurality of output values and estimation values in the present, past, and future are used, a case where a plurality of output values and estimation values of different views are used, and the like. However, it is desirable that an angle difference between the views to be used is within a few degrees.

«Other Change Example»

Although a blurring process is performed for a value after LOG conversion in the first embodiment, an addition process is performed after inverse conversion of the LOG conversion, and then the LOG conversion may be performed again.

Also, although the defective element correction S330 was performed after the air correction S320 as shown in FIG. 3, the defective element correction may be performed, for example, before the offset correction S300, between the offset correction S300 and the LOG conversion S310, between the LOG conversion S310 and the air correction S320, and the like. Additionally, in a case where there are not a couple of processes of FIG. 3 other than the defective element correction S330 and a case where the other processes are additionally added to FIG. 3, the processes may be performed in any order before the reconstruction calculation S340.

The change examples of the first embodiment described above can be combined each other as needed unless there is no technical contradiction. Also, the change examples can be applied to the other embodiments to be described later.

<Second Embodiment>

The present embodiment is characterized by providing a blurring process controller. That is, the central processing unit 105 is provided with a correction controller that controls a blurring amount or a blurring rate with a blurring processing part in the present embodiment. The correction controller controls a blurring amount or a blurring rate according to the position of a defective element in the detector, the size of a radiation focus for irradiating a radiation to the detector, and the conditions such as an output noise ratio (SNR) of the detector.

Figure 10:
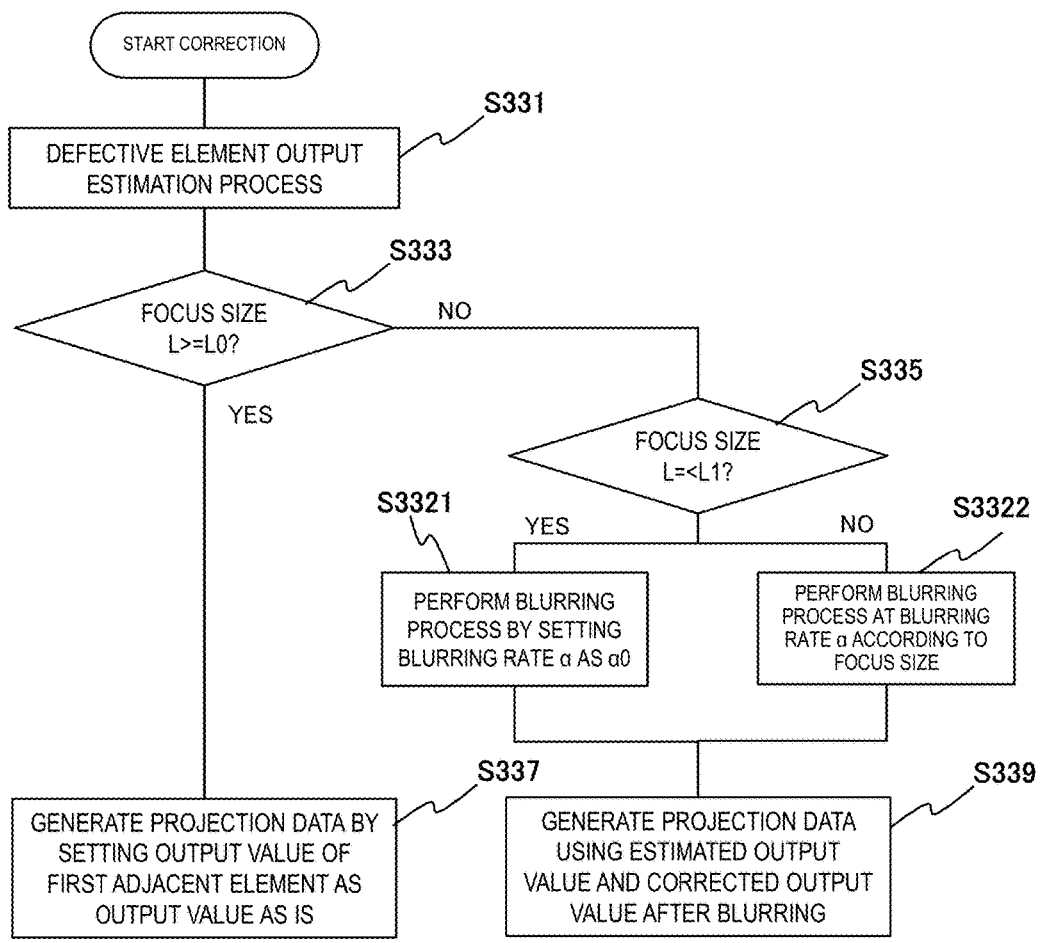
FIG. 10 is a flow showing the procedure of the defective element correction in the second embodiment.

That is, the second embodiment is characterized by not similarly performing a blurring process for a first adjacent element adjacent to a defective element but changing whether or not there is a blurring process and a blurring degree according to the device conditions and the other factors. Hereinafter, controlling of the blurring process according to the focus size that is a typical factor will be described. The other processes are similar to the above first embodiment and the change examples, the repeated descriptions are omitted, and the contents of the blurring process S332 shown in FIG. 3 will be mainly described in detail by referring to FIG. 10. FIG. 10 is a flow showing the processes of the defective element correction S330 in the second embodiment.

First, the defective element output estimation process S331 is performed. This process is similar to an estimation process in the first embodiment. An output value in a position (pixel) of a defective element obtained from the defective element map is estimated using output values of normal elements adjacent to the position in the channel direction, slice direction, or oblique direction or a combination of output values of these normal elements. As the estimation method, the linear interpolation shown in the formula (2) or an estimation using the other function may be used.

Next, whether or not to perform a blurring process is determined depending on the focus size (the first determining step S333), the procedure proceeds to the second determining step S335 in case of performing the blurring process, and the procedure proceeds to the process S337 in case of not performing the blurring process. Determining whether or not to perform the blurring process depends on the focus size (size of an X-ray focus) when irradiating an X-ray from the X-ray source 100.

A general X-ray CT apparatus can switch a plurality of focus sizes during the use, and a focus size is selected via the input unit 119. The central processing unit 105 uses information of the selected focus size to perform the determination S333.

When the focus size L is large as shown in FIG. 11(a), a part of the X-ray that is irradiated from the focus 162, is transmitted through the scanning object 163, and is incident on the defective element 165 is also incident on the adjacent elements 164 and 166 similarly to the defective element 165. Here, the X-ray range W is a range where the X-ray 168 that is irradiated from the focus 162 and transmitted through the scanning object 163 to the X-ray detector 104 is incident on the X-ray detector 104. Therefore, because output values of the adjacent elements 164 and 166 includes information to be input to the defective element 165, an output estimation of the defective element 165 using these values can achieve a high accuracy, which results in that a blurring correction may not be required or that a blurring rate may be small. Such a focus size L0 for which a blurring process is not required is a focus size at which artifacts are not generated without performing the blurring correction and can be calculated in previous scanning. Alternatively, a focus size at which the X-ray range W is equal to all the regions of the adjacent elements 164 and 166 can be calculated as L0.

On the other hand, when the focus size L is smaller than L0, a rate of an X-ray incident on the adjacent elements 164 and 166 is reduced from among X-rays transmitted through the scanning object 163, which result in a low accuracy of output estimation for the defective element 165 using an output of an adjacent element. Therefore, it is desirable to perform a blurring process. Particularly, when the focus size of an X-ray is small enough as shown in FIG. 11(*b*), an X-ray transmitted through the scanning object 163 is not incident on the adjacent elements 164 and 166, which results in that a large blurring amount of blurring correction is required due to a low output estimation accuracy.

Therefore, when it is determined as NO (L<L0) i.e., to perform a blurring process in the first determining step S333, whether or not the focus size L is equal to or less than the predetermined lowest value L1 is further determined (the second determining step S335). The procedure proceeds to the blurring process S3321 when it is determined that the focus size L is equal to or less than the lowest value L1, and the procedure proceeds to the blurring process S3322 when the focus size L is larger than the lowest value. The lowest value L1 of the focus size is a sufficiently small value to which an estimation accuracy does not depend on the focus size. The lowest value L1 can also be calculated in previous scanning similarly to L0.

Alternatively, for example, a focus size at which the X-ray range W is the same as a defective element size may be set as L1.

Either of the blurring process S3321 or S3322 corrects an output value of a first adjacent element with the formula (3) or (4) using an output value of the first adjacent element for the blurring process, an estimated output value of a defective element, and an output value of a second adjacent element adjacent to the first adjacent element similarly to the first embodiment. However, in the blurring process in a case where the focus size L is equal to or less than the lowest value L1, a certain blurring rate α0 set as a blurring rate α in advance is used. The blurring rate α0 can be calculated previously together with the lowest value L1 of the focus size in previous scanning.

In the blurring process S3322, the formula (3) or (4) is applied using a different blurring rate α according to the focus size. That is, in the range where the focus size is from L0 to L1, an irradiation range including the adjacent elements 164 and 166 is reduced linearly to the focus size, and the blurring rate α in this range is changed for the focus size L linearly like the formula (7), for example.

[Formula 7]

$$\alpha = \frac{L - L_0}{L_1 - L_0} \alpha_0 \text{ (in case of } L_1 \leq L \leq L_0\text{)} \quad (7)$$

Additionally, the blurring rate α may be set as various functions at a linear focus size without changing linearly for the focus size or a previously determined value may be used without using the functions.

Projection data is generated by setting a corrected output value of a first adjacent element after the blurring processes S3321 and S3322 as an output value of the first embodiment and setting an estimated output value as an output value of a defective element (the process S339). In a case where a blurring process is not performed because the focus size L is equal to or more than the predetermined value L0 (or the blurring rate is set to 0), an output value of the first adjacent element is used as is, and the projection data is generated using the estimated output value for the defective element (the process S337). Reconstructing an image from the projection data is similar to the first embodiment, and the description will be omitted.

According to the present embodiment, by adjusting whether or not to perform a blurring process and the degree according to the focus size, artifacts can be prevented from being generated due to an unnecessary blurring process, as well as an optimal blurring process can be performed according to the estimation process accuracy.

Additionally, the determination method of the above blurring rate is just an example and does not limit the present invention. For example, although the described here are cases of performing different processes respectively by setting two threshold values L0 and L1 and dividing a focus size range into three, only whether or not to perform a blurring process may be adjusted by simply setting one threshold value or it may be configured so that a blurring rate is changed in a predetermined range without determining whether or not to perform a blurring process. Also, the blurring process may be performed at all the focus sizes from among a plurality of switchable focus sizes or a blurring correction may be performed only at a partial focus size. For instance, if a large focus and a small focus can be changed each other, the central processing unit 105 performs the blurring process S332 in the defective element correction S330 when the small focus is selected from the input unit 119, and there can be a case where the blurring process S332 is not performed in the defective element correction S330 when the large focus is selected. Also, there can be a case where a blurring rate is changed before the use according to the focus size, and the blurring rate may be reduced in case of the large focus.

Also, although an example of changing whether or not to perform a blurring process and a blurring rate according to the focus size was described in the above embodiment, whether or not to perform a blurring process and a blurring rate may be changed according to the size and the site of the object 102 to be scanned. The scanning object 163 of FIG. 1 is equivalent to a site or a part of the object 102, and an amount of which an X-ray similar to the defective element 165 is incident on the adjacent elements 164 and 166 varies according to the position and the size.

Additionally, because an amount of artifacts to be generated and the visibility varies according to the image and reconstruction filters to be used in scanning, the tube current, the tube voltage, the position of a defective element, the number of projection data to be used for generating a reconstructed image, and the like, whether or not to perform a blurring process and a blurring rate may be changed.

<Third Embodiment>

Also in the present embodiment, the defective element correction includes the defective element output estimation process and the blurring process similarly to the first embodiment. The present embodiment is different from the first embodiment in the output estimation method of the defective element output estimation process S331 and in providing a limit to the blurring process S332. That is, the central processing unit (the blurring processing part) of the third embodiment estimates a gap amount from a true value of an estimated output value estimated by an estimation part using output values of detection elements in rows and/or columns adjacent to a row and/or column including a defective element for which the estimated output value is estimated from among a plurality of detection element arrays in order to adjust the blurring amount and blurring rate according to the said gap amount.

Hereinafter, the processes of the present embodiment different form the first embodiment will be mainly described in detail.

«Defective Element Output Estimation Process S331»

First, the defective element output estimation process S331 estimates a gap between an output value of a defective element calculated by interpolation and the original output value to estimate the defective element output value by considering the gap amount. The estimated output value for which the estimated gap (referred to as an estimated gap amount) was considered can be expressed as the formula (8) by setting a defective element position as (m, n) and setting an estimated gap amount for the defective element as $\Delta(m, n)$, for example.

[Formula 8]

$$Q(m,n) = \tfrac{1}{2}(P(m-1,n) + P(m+1,n)) - \Delta(m,n) \quad (8)$$

The first term on the right side of the formula (8) is equal to the right side of the formula (2) and is a value interpolating an output value of a defective element from output values P(m, n−1) and P(m, n+1) of the first adjacent elements adjacent to the defective element.

As shown in FIG. 12(a), when an output value of the defective element S2 in a position (m, n) is estimated from the two normal elements S1 and S3 adjacent to the defective element S2 by linear interpolation, there can be a gap between the estimated output value and the original output value of the defective element S2.

In the present embodiment, a gap amount $\Delta(m, n)$ is calculated using output values of the corresponding normal elements in a row or column different form the normal elements S1 and S3 used for the estimation. The different row or column is an adjacent slice or an adjacent channel typically. FIGS. 12(b) and 12(c) show output values of the detection elements corresponding to the row or column different from the detection elements S1 to S3 shown in FIG. 12(a). In the following description, as an example, the first adjacent elements S1 and S3 are elements adjacent in the channel direction in the same slice as the defective element S2, and a case where a gap amount is estimated from the elements S11 and S13 as well as the elements S21 and S23 corresponding to slices on both sides adjacent to the above slice in order to use for output estimation of the defective element will be described.

Therefore, first, output values of the first adjacent elements S1 and S3 adjacent to the defective element S2 are used similarly to the first embodiment in order to calculate an estimated output value of the defective element S2 by the formulas (2) and (3), for example. The estimated output value is set as a temporary estimation value.

The similar calculation is performed for the two elements (S11 and S13 of FIG. 12(b)) corresponding to the first adjacent elements S1 and S3 in the other slice (the channel number is the same) in order to perform output estimation of the element (S12 of FIG. 12(b)) between the two elements. The difference between an estimated output value Q(m, n−1) and an output value P(m, n−1) of the element S12 is a gap amount $\Delta(m, n-1)$. Similarly, also for the corresponding elements (S21 and S23 of FIG. 12(c)) in the other slice, the difference between an estimated output value Q(m, n+1) of the element S22 located between the above elements and an actual output value P(m, n+1) is calculated as a gap amount $\Delta(m, n+1)$. The calculation for a gap amount from two elements adjacent in the slice direction can be expressed together by the formula (9).

[Formula 9]

$$\Delta(m, n+i) = \frac{P(m-1, n+i) + P(m+1, n+i)}{2} - P(m, n+i) \quad (9)$$

In the formula, "i=+−1" is applied (hereinafter, it is the same).

Using the calculated gap amounts $\Delta(m, n-1)$ and $\Delta(m, n+1)$ of adjacent slices, a gap amount $\Delta(m, n)$ of the defective element S2 for which output estimation is performed is calculated by the formula (10).

[Formula 10]

$$\Delta(m, n) = \frac{\Delta(m, n-1) + \Delta(m, n+1)}{2} = \\ \frac{P(m-1, n-1) + P(m+1, n-1) - 2Q(m, n-1) + P(m-1, n+1) + P(m+1, n+1) - 2Q(m, n+1)}{4} \quad (10)$$

An estimated output value of the defective element S2 can be calculated from the gap amount $\Delta(m, n)$ calculated in the formula (10) and the formula (8).

The above described calculation method is used in a case where the defective element S2 is not an end in the slice direction, but in a case where the defective element is an end slice, an estimated gap amount $\Delta(m, n+j)$ calculated from slices adjacent to the slice may be used as the estimated gap amount $\Delta(m, n)$, for example. The estimated gap amount $\Delta(m, n)$ at this time can be expressed as the formula (11) instead of the formula (10).

[Formula 11]

$$\Delta(m, n) = \\ \Delta(m, n+j) = \frac{P(m-1, n+j) + P(m+1, n+j)}{2} - Q(m, n+j) \quad (11)$$

As the other method, in a case where a defective element is in an end slice, the estimated gap amount $\Delta(m, n)$ may be considered as 0.

Also, for example, in a case where output values cannot be obtained because any of the output values of elements adjacent in the slice direction that are used for calculating a gap amount is a defective element in an output estimation process, output values of the next adjacent elements may be used, or alternatively either output value of the element pair in the slices on both sides may be used. Also, although a case where a temporary estimated output value and an estimated output value are calculated using output values of the first adjacent elements adjacent in the channel direction was described in the above description, the temporary estimated output value calculation can be performed using combinations of various normal elements as described in the first embodiment and the change examples.

Also, although a case where an estimated gap amount is calculated in adjacent slices was described, this is just an example, and an output value of a slice distant by a plurality of slices may be used.

«Blurring Process»

Figure 13:
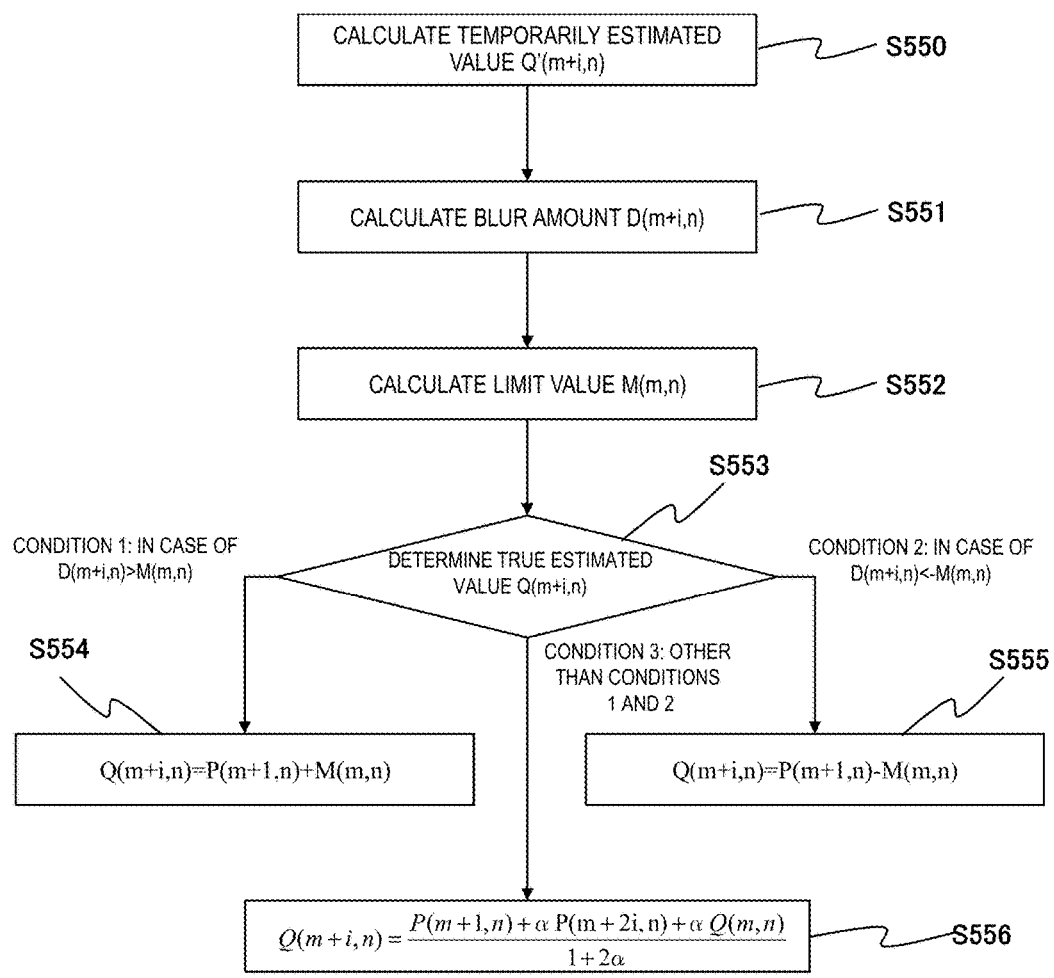
FIG. 13 is a flow showing the procedure of the blurring process in the third embodiment

In the blurring process S332, a blurring amount is restricted by a predetermined limit value, and then a corrected output value Q(m+i, n) of a first adjacent element is determined in a range limited by the limit value. The processing procedure will be described by referring to FIG. 13.

First, a temporary corrected output value Q'(m+i, n) of the first adjacent element is calculated (S550). This calculation method is, for example, the same as that of a corrected output value Q(m+i, n) in the first embodiment and uses the formula (3) during the calculation. Next, a blurring amount D(m+i, n) is calculated (S551). The blurring amount D(m+i, n) is a difference between a temporary corrected output value and a true output value and can be expressed by the formula (12).

[Formula 12]

$$D(m,n+i)=Q'(m,n+i)-P(m,n+i) \qquad (12)$$

On the other hand, a limited amount M(m, n) of a blurring amount is calculated (S552). This amount restricts a blurring amount in the blurring process S332 for each defective element and is set as a function of the estimated gap amount $\Delta(m, n)$ of the defective element that was calculated in the estimation process S331. As shown in FIG. 12 and the formula (8), the estimated gap amount $\Delta(m, n)$ indicates a gap amount of linear interpolation for the defective element, and a large gap amount means that an estimation accuracy by the linear interpolation is reduced. If a gap amount of the linear interpolation for the defective element is large, it is highly possible that a blurring process accuracy is reduced when a value of a first adjacent element is calculated by the linear interpolation (the formula (3)) in the blurring process S332. Therefore, if the estimated gap amount $\Delta(m, n)$ is large, the limited amount M(m, n) is reduced to prevent wrong correction because it is highly possible that wrong interpolation is performed.

Therefore, a function in which a limited amount is reduced when the estimated gap amount $\Delta(m, n)$ is large is available as shown in the formula (13), for example.

[Formula 13]

$$M(m,n)=|A-B\cdot\Delta(m,n)| \qquad (13)$$

A and B are constants in the formula (13) and can be determined in advance by image quality evaluation before actual scanning.

Although the above function is that in a case where a limited amount M(m, n) changes linearly to an estimated gap amount $\Delta(m, n)$, various functions can be adopted. That is, the limited amount can be expressed by the generalized formula (14).

[Formula 14]

$$M(m,n)=g(\Delta(m,n)) \qquad (14)$$

As a function "g" of the formula (14), various functions such as a polynomial, a trigonometric function, an exponential function, and a logarithmic function can be adopted. Also, various step functions in which a value is determined for each threshold value may be adopted. Particularly, because it is thought that an accuracy of the blurring process S332 is considerably reduced when an estimated gap amount $\Delta(m, n)$ is equal to or larger than a certain value, it is useful to determine the function "g" so that a limited amount M(m, n) becomes zero. Also, the limited amount M(m, n) may be determined from an estimated gap amount $\Delta(m, n)$ using a previously prepared table.

Next, the limited amount M calculated in the above process S552 and the blurring amount D calculated in S551 are compared to determine a true corrected output value Q(m+i, n) of a first adjacent element (S553). In this determination process, the comparison result is divided into three conditions to determine a corrected output value Q for each condition. First, when a blurring amount D(m+i, n) is larger than the limited amount M(m, n) (condition 1), the limited amount M(m, n) is added to an output value P(m+i, n) of the first adjacent element to set as the corrected output value Q(m+i, n) (S554). That is, the blurring amount is restricted to the limited amount M(m, n). When the blurring amount D(m+i, n) is smaller than –M(m, n) (condition 2), –M(m, n) is added to the output value P(m+i, n) to set as the corrected output value Q(m+i, n) (S555). That is, the blurring amount is restricted to –M(m, n). In case of other than the conditions 1 and 2 (condition 3), a temporary corrected output value Q'(m+i, n) calculated from the formula (3) is set as a corrected output value as is.

Additionally, although a limited amount common to all the first adjacent elements adjacent to a defective element may be used for the limited amount M, the respective limited amounts can be applied by calculating them separately.

As described above, the blurring process of the present embodiment restricts a blurring amount D to a range from –M to M to reduce unnecessary blur by providing a limit based on a gap amount to a correction amount (blurring amount) of an output value of a first adjacent element, which can prevent artifacts from generating in a reconstructed image.

Although a blurring amount D is determined using a limited amount M(m, n) here, this results in determining a blurring rate $\alpha$ (the formula (3)) using the limited amount, which can be regarded as an example of a method to change the blurring rate $\alpha$.

As an example of the effect of the present embodiment, the image 148 in which a limited amount is not provided to the blurring process and the image 149 in which a limited amount is provided are shown in FIG. 14. Both the images show reconstructed images of a head phantom. These images are generated by artificially generating a defective element and performing the defective element correction S330 for the raw data 143 that had no defective elements and was acquired by scanning with the X-ray detector 104, and the defective element output estimation process S331 as well as the blurring process S332 are performed for both the images. Because the artifacts shown in the arrow in the image 148 are reduced in the image 149, the effect of providing a limited amount can be understood.

<Change Example of Third Embodiment>

«Change Example of Output Estimation Process»

Although a temporary estimated output value of a defective element is interpolated and calculated using an output value of an element adjacent in the channel direction and an estimated gap amount is calculated using an output value of an adjacent slice in the third embodiment, this is just an example, the interpolation of the defective element may be performed using a value in the slice direction, and the estimated gap amount may be calculated using an output value of an adjacent channel, for example. Additionally, there can be various cases where a temporary estimated output value and an estimated gap amount are calculated from an output value and a correction amount of different sets of elements. At this time, a common element may be included in these sets. There may be cases where an element belonging to both the directions of the channel and the slice is used and where elements around the defective element are used.

Although a temporary estimated output value and a gap amount are calculated by linear interpolation in the third embodiment, this is just an example and does not limit the present invention. For example, various interpolations such as a polynomial interpolation and a non-linear interpolation may be used. In this case, the same interpolation is used for the first term of the formula (9) to calculate an estimated gap amount Δ(m, n+1). Also, a temporary estimated output value may be calculated by fitting using linear and higher-order functions etc. At this time, the same fitting is performed for the first term of the formula (9).

That is, when a function to determine a temporary estimated output value is set as the function h and an output value of sets of elements to be used for the calculation is set as $p_k(m, n)$ (k: the number of used data, the same shall apply hereinafter.), an estimated output value Q(m, n) of a defective element can be calculated using the formula (15) instead of the formula (8).

[Formula 15]

$$Q(m,n) = h(p_k(m,n)) - \Delta(m,n) \quad (15)$$

At this time, an estimated gap amount Δ(m, n) can be calculated from an estimated gap amount Δ(M, N) (M and N are integers.) at an element (a position (M, N)) adjacent to the defective element. On the other hand, the gap amount Δ(M, N) can be calculated from the formula (16) derived by considering similarly to the formula (9) case.

[Formula 16]

$$\Delta(M,N) = h(p_k(M,N)) - P(M,N) \quad (16)$$

In the formula (16), P(M, N) shows an output value of an element in a position (M, N), and $p_k(M, N)$ shows an output value of sets of elements corresponding to an output value "$p_k(m, n)$" of sets of elements used for calculating a temporary correction value when the element in a position (M, N) is displaced in a position of a defective element.

Also, as a calculation method for an estimated gap amount Δ(m, n), there is a method for calculating as an average value of an estimated gap amount Δ(M, N) of an element adjacent in the slice direction as shown in the formula (10), for example.

However, the present invention is not limited to this, and there can be a case of using an element adjacent in the channel direction, a case of using both the elements in the channel and slice directions, a case of using elements around a defective element, and the like. Additionally, there are not only a case of averaging estimated gap amounts of these elements but also a case of determining by fitting using a function. Additionally, "$p_k(m, n)$" is not limited to an output value of the same view as a view for which an estimated gap amount Δ(M, N) was calculated, may be output values of the past and future views i.e., views with different view angles and different periods, and may also be output values of two or more views of the present, past, and future.

«Change Example of Limited Amount Calculation Method»

Although a limited amount M restricting a blurring amount in a blurring process is set as a function of an estimated gap amount of an estimated output value of a defective element in the third embodiment, the limited amount M may be functions of an estimated output value Q of a defective element and output values of pixels around the defective element. Also, the limited amount M may be functions of a change amount of the estimated output value of the defective element and a change amount of an output value of the other pixel. Noise and SNR are an example of the change amount here. By thus determining the function, an appropriate limited amount M can be determined. For example, when SNR is high due to a large amount of incident radiation on a detector, artifacts in a reconstructed image can be found much easier. Therefore, the artifacts can be reduced by providing a small limited amount M to reduce the blurring amount.

An amount of incident radiation on a detector can be calculated from output and a change amount of a reference detector. The reference detector is that disposed in a position on which an X-ray irradiated from the X-ray source 107 is directly incident without transmitting through an object in a normal manner and may be a part of the X-ray detector 104 or be provided separately. By using a signal of such a reference detector, a limited amount M can be determined according to the irradiation X-ray amount. Also, there can be a case where the limited amount M is calculated using output values and estimation values of elements of various views including the past and present views.

«Change Example of Estimated Gap Amount to be Used for Blurring Process»

Although an estimated gap amount Δ calculated in the defective element output estimation process S331 is used as an estimated gap amount for calculating a limited amount in the blurring process S332 in the third embodiment, an estimated gap amount Δ for the blurring process S332 may be calculated separately. This may be calculated from the other elements, and for example, an estimated gap amount Δ calculated using the various surrounding elements including a second adjacent element may be used. Also, the calculation may be performed using a formula other than the formulas (9) and (10) shown above, corrected output values are calculated for one or more elements (excluding a defective element) such as elements around a first adjacent element, elements around the other defective element, second adjacent elements to be used for the blurring process S332, and elements around the second adjacent elements using the formula (3), and then an estimated gap amount Δ for the blurring process S332 may be calculated from a gap amount between the output values of the elements.

Also, similarly to a case of a defective element, a corrected output value (estimation value) is calculated using not an output value of the element but an output value of a surrounding element, and then an estimated gap amount Δ for the blurring process S332 may be calculated from a difference between the corrected output value and an estimated output value calculated in the defective element output estimation process S331. Additionally, the calculation method for the corrected output value is not limited to the formula (3).

However, as described in the third embodiment, in a case of using an estimated gap amount Δ(m, n) calculated in the defective element output estimation process S331 as an estimated gap amount for calculating a limited amount in the blurring process S332, it takes a shorter time for the calculation etc. than a case of calculating separately, which results in an advantage capable of reducing the memory to be used.

«Change Example of Blurring Process»

Although a method for restricting a blurring amount in the blurring process S332 by providing a limited amount is described in the third embodiment, the purpose of the third is to restrict the blurring amount in consideration with various factors on artifact generation, the method is not limited to this, and various methods can be adopted.

For example, a blurring rate α shown in the formula (3) may be changed directly. At this time, the blurring rate α may be set as a function of, for example, an estimated gap amount Δ(m, n) similarly to a case of a limited amount M(m, n) and may also be set as functions of an estimated output value Q(m, n) of a defective element, output values of the surrounding pixels of the defective element, the estimated output value of the defective element as well as output values of the other pixels and the change amount, and functions of an output value, the change amount, and the like of a reference detector.

<Other Embodiment of Radiation Imaging Device>

Although the embodiments in which the present invention is applied to a medical X-ray CT apparatus are described in the above first to third embodiments, the present invention is not limited to this and can be applied to all apparatuses equipped with a detector in which a lot of detection elements detecting an X-ray are arranged and a central processing unit correcting an output value of a defective element included in the detector. For example, the present invention can be applied to an X-ray CT apparatus for non-destructive examination, X-ray cone beam CT apparatus, dual energy CT apparatus, X-ray image diagnosis apparatus, X-ray image scanning apparatus, X-ray fluoroscopic apparatus, mammography apparatus, digital subtraction apparatus, nuclear medicine examination apparatus, radiation therapy apparatus, and the like. Any type of detector detecting radiations with various wavelengths such as an X-ray, visible ray, infrared ray, ultraviolet ray, gamma ray, and the like can be adopted.

<Embodiment of Image Processing Device>

The present invention includes an image processing device that does not include a detector but processes output data of the detector to generate image data. Hereinafter, the embodiment of the image processing device will be described. The image processing device of the present embodiment comprises an image generation unit generating an image using projection data comprised of output values of a plurality of the respective detection elements arranged in a detector and a data correction unit correcting imperfection of the projection data due to a defective element included in the detector.

The data correction unit comprises an estimating part estimating an output value of a defective element and a blurring processing part performing a blurring process for output values of detection elements located around a defective element using an estimated output value estimated for the said defective element and performs correction by setting the estimated output value as the output value for the defective element and setting an output value after the blurring process as the output value for the detection elements for which the blurring process was performed. The image generation unit generates an image using projection data corrected by the data correction unit.

The image processing device of the present embodiment can be comprised of a central processing unit and a user interface (UI) for displaying and inputting, for example. The image processing unit inputs output data collected by a detector of an image scanning apparatus directly from the image scanning apparatus and through communication, portable media, or the like and information (a defective element map) about the defective element of the detector to perform defective element correction. Output data to be loaded by the image processing device may be raw data from the detector or data for which offset correction, air correction, or the like was performed.

Figure 15:
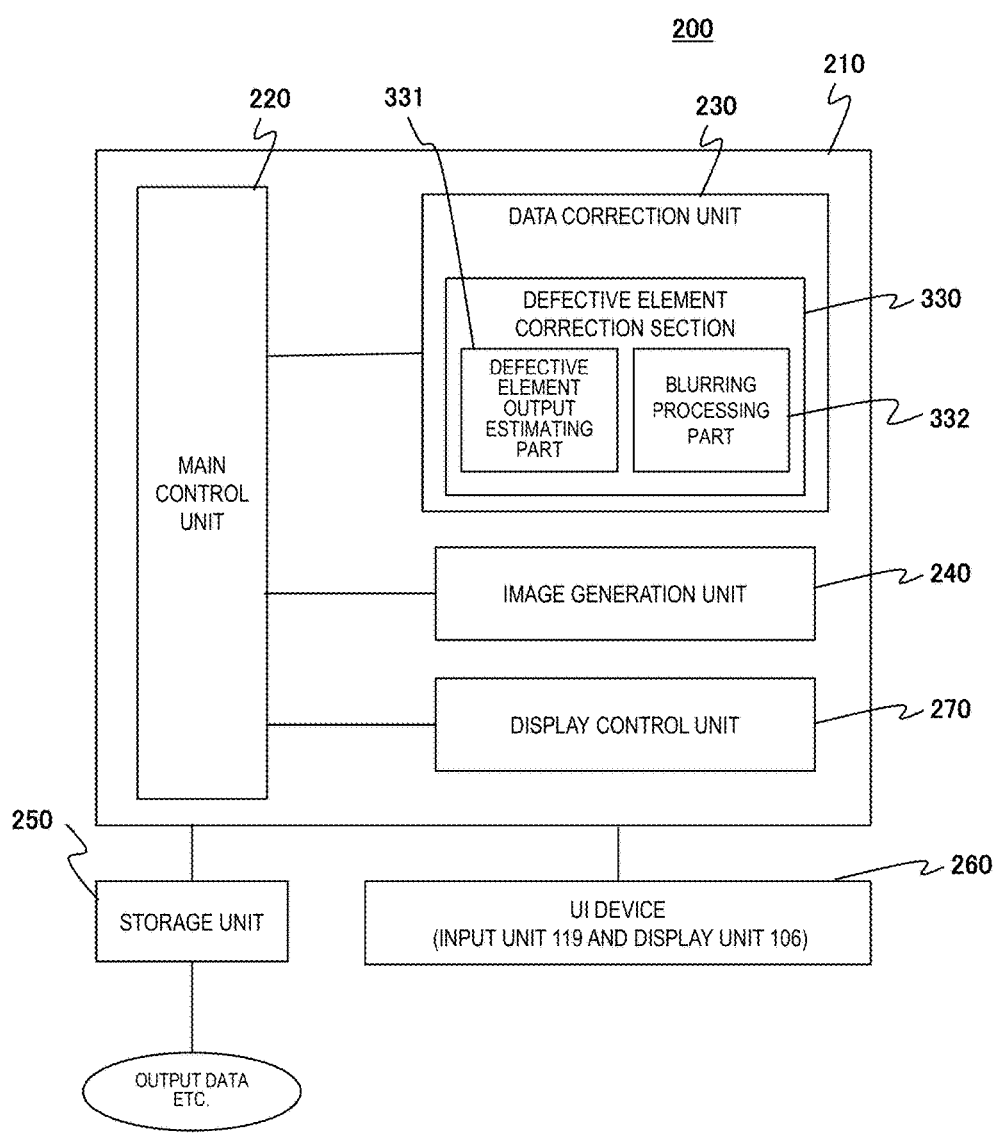
FIG. 15 shows an example of the functional block diagram of the image processing device.

An example of the functional block diagram of the image processing unit is shown in FIG. 15. The image processing device 200 shown in the diagram comprises the central processing unit 210, the storage unit 250, and the UI device 260 (equivalent to the display unit 106 and the input unit 119) to be connected to the central processing unit 210 as needed. The central processing unit 210 is comprised of the main control unit 220, the data correction unit 230, the image generation unit 240, and the like and includes the display control unit 270 too in a case where the image processing device 200 includes the display unit 106.

The data correction unit 230 performs various types of correction for input data according to the property of the data comprises the defective element correction section 330. The data comprises the defective element correction section 330 is comprised of the defective element output estimating part 331 and the blurring processing part 332.

The defective element output estimating part 331 performs output estimation of a defective element using positional information and output data of the defective element map 142. The blurring processing part 332 performs a blurring process for output values of the elements around the defective element using the estimated output value of the defective element that was estimated by the defective element output estimating part 331 and the output values of the surrounding elements (or the estimated output values). Whether or not to perform the blurring process and the degree are adjusted according to the degree of artifacts that can be generated. Conditions etc. necessary for these processes are set or input through the UI 260. These processes of the defective element output estimating part 331 and the blurring processing part 332 are as described in the above first to third embodiments, and the repeated descriptions will be omitted.

The image generation unit 240 generates projection image data using output data corrected by the defective element correction section 330. In a case where output data is comprised of a plurality of data with different rotation angles (views) like an X-ray CT apparatus etc., a calculation such as a convolution is performed for a plurality of projection data (corrected projection data) to reconstruct a tomographic image. When an image processing device is provided with the display unit 106, the reconstructed image data is converted into display data on which the other necessary display information was superimposed in the display control unit 270 and is displayed on the display unit 106. Also, the reconstructed image data is forwarded to the other display device and imaging device or stored in a storage unit as needed.

The image processing device of the present embodiment can process output data from a plurality of different radiation imaging devices and can obtain the effects of the present invention without changing an existing radiation imaging device. Also, diverse applications such as processing an image from an imaging device in a remote location and sending it back to the remote location can be provided.

The blurring processing part 332 of the image processing device of the present embodiment may be provided with a correction controller that controls a blurring amount or a blurring rate. The correction controller may control a blurring amount or a blurring rate using an estimated output value of a defective element similarly to the second and third embodiments and may control a blurring amount or a blurring rate using output values of detection elements located around the defective element and an estimated output value.

Although various embodiments and change examples of the present invention are described above, the present invention is not limited to the above embodiments and can be performed by changing variously within the scope of the gist in the implementation stage. Additionally, the above embodiments include various stages, and various inventions can be extracted by appropriately combining a plurality of disclosed constituent elements. For example, some constituent elements may be deleted in all of the constituent elements disclosed in the embodiments.

Industrial Usability

According to the present invention, artifacts can be reduced by estimating an output value of a defective element in a detector having the defective element, and additionally, artifacts remaining due to an estimation gap of the defective element can be reduced so that they are inconspicuous.

DESCRIPTION OF REFERENCE NUMERALS

100: X-ray CT apparatus (image scanning apparatus)
107: X-ray source
101: gantry rotation unit
102: object
103: bed top plate
104: X-ray detector
105: central processing unit
106: display unit
109: storage unit
116: X-ray collimator
117: control unit
118: signal collection unit
119: input unit
330: defective element correction section
331: defective element output estimating part
332: blurring processing part
142: defective element map
143: raw data
144: projection data
145: reconstructed image
146 to 149: reconstructed images

The invention claimed is:

1. An image processing device comprising:
an image generation unit that generates an image using projection data composed of output values of the respective detection elements of a detector composed by arranging
a plurality of detection elements; and
a data correction unit that corrects the incompleteness of the projection data due to a defective element included in the detector,
wherein the data correction unit comprises an estimating part that estimates an output value of the defective element and a blurring processing part that performs a blurring process for output values of the detection elements located around the said defective element using an estimated output value estimated for the defective element and sets the estimated output value as an output value for the defective element to perform correction for the detection elements using output values after the blurring process, and
the image generation unit generates the image using the projection data corrected by the data correction unit, and
wherein the estimating part calculates an estimated output value of the said defective element using output values of the first adjacent elements located around the defective element, and
the blurring processing part performs a blurring process using a value for which a first blurring rate is multiplied by an estimated output value estimated for the defective element, output values of the first adjacent elements, and a value for which a second blurring rate is multiplied by output values of the second adjacent elements other than the defective element that are located around the first adjacent elements.

2. The image processing device according to claim 1, further comprising:
a correction controller that controls a blurring amount or a blurring rate with the blurring processing part.

3. The image processing device according to claim 2,
wherein the correction controller controls a blurring amount or a blurring rate using at least either one of output values of the first adjacent elements located around the defective element, output values of the second adjacent elements located around the first adjacent elements, and an estimated output value of the defective element to be calculated using the output values of the first adjacent elements.

4. The image processing device according to claim 3,
wherein the detector includes a plurality of detection elements arranged in a first direction and a second direction crossing the said first direction, and
the blurring processing part estimates a gap amount of an estimated output value estimated by the estimation part from a true value using output values of detection elements in rows and/or columns adjacent to a row and/or column including a defective element for which the estimated output value is estimated from among the plurality of detection element arrays in order to adjust the blurring amount or blurring rate according to the said gap amount.

5. The image processing device according to claim 2,
wherein the correction controller controls the blurring amount or the blurring rate according to the conditions including any of a position of the defective element in the detector, a size of a radiation focus for irradiating a radiation to the detector, and an output noise ratio of the detector.

6. The image processing device according to claim 5,
wherein the correction controller is provided with an input unit that inputs the blurring amount or the blurring rate as well as the conditions to determine the blurring amount or the blurring rate.

7. The image processing device according to claim 1,
wherein the estimating part calculates an estimated output value of the said defective element using output values of the first adjacent elements located around the defective element, and
the blurring processing part calculates a blurring amount using at least either one of an estimated output value estimated for the defective element or output values of the second adjacent elements other than the defective element that are located around the first adjacent elements and performs a blurring process by adding the blurring amount to the output values of the first adjacent elements.

8. The image processing device according to claim 1,
wherein the detector includes a plurality of detection elements arranged in a first direction and a second direction crossing the said first direction, the estimating part estimates an estimated output value of the defective element using output values of detection elements adjacent to the defective element in the first direction and/or output values of detection elements adjacent to the defective element in the second direction, and the blurring processing part performs a blurring process for output values of detection elements used for estimating the estimated output value by the estimating part.

9. A radiation imaging device comprising:

the image processing device according to claim 1, wherein a radiation source, a detector that is disposed opposite to the said radiation source and composed by arranging a plurality of detection elements, and an image generation unit that generates an image to be examined based on output values of the respective detection elements of the detector are provided.

10. The radiation imaging device according to claim 9, wherein the radiation imaging device is an X-ray CT apparatus.

11. The radiation imaging device according to claim 10, wherein the data correction unit performs estimation of an estimated output value by the estimating part and a blurring process by blurring processing part for a part of projection data from among a plurality of the projection data with different positions in the rotation direction of the detector and corrects all the rest of the projection data with different positions in the rotation direction by using the estimated output value estimated for the part of the projection data and a blurring amount used for the blurring process.

12. An image processing device comprising:

an image generation unit that generates an image using projection data composed of output values of the respective detection elements of a detector composed by arranging a plurality of detection elements; and a data correction unit that corrects the incompleteness of the projection data due to a defective element included in the detector, wherein the data correction unit comprises an estimating part that estimates an output value of the defective element and a blurring processing part that performs a blurring process for output values of the detection elements located around the said defective element using an estimated output value estimated for the defective element and sets the estimated output value as an output value for the defective element to perform correction for the detection elements using output values after the blurring process, and the image generation unit generates the image using the projection data corrected by the data correction unit, wherein the detector includes a plurality of detection elements arranged in a first direction and a second direction crossing the said first direction, the estimating part estimates an estimated output value of the defective element using output values of detection elements adjacent to the defective element in the first direction and/or output values of detection elements adjacent to the defective element in the second direction, and the blurring processing part performs a blurring process for output values of detection elements used for estimating the estimated output value by the estimating part, and wherein the blurring processing part estimates a gap amount from a true value of an estimated output value estimated by the estimation part using output values of detection elements in rows and/or columns adjacent to a row and/or column including a defective element for which the estimated output value is estimated from among the plurality of detection element arrays in order to adjust a blurring amount or a blurring rate according to the said gap amount.

13. An image processing method for generating an image using output values of the respective detection elements of a detector composed by arranging a plurality of the detection elements, including:

a step of estimating an output value of a defective element included in the detector using output values of the respective detection elements other than the defective element around the said defective element;

a step of performing a blurring process for output values of the detection elements around the said defective element using an estimated output value estimated for the defective element;

a step of setting a blurring amount or a blurring rate used for the said blurring process; and a step of generating the image using the estimated output value and the output values after the blurring process respectively for the defective element and the detection elements for which the blurring process is performed, wherein the step of setting a blurring amount or a blurring rate includes a step of estimating a gap amount between an estimated output value of the defective element and the true output value and a step of setting a limit value of the blurring amount or the blurring rate using the estimated gap amount, and the step of performing the blurring process uses the blurring amount or the blurring rate limited by the limit value.

14. The image processing method according to claim 13, further including:

a step of determining whether or not to perform the blurring process before the step of performing the blurring process.

* * * * *